(12) United States Patent
Elanany et al.

(10) Patent No.: US 10,189,986 B2
(45) Date of Patent: Jan. 29, 2019

(54) ACRYLAMIDE-BASED COPOLYMERS, TERPOLYMERS, AND USE AS HYDRATE INHIBITORS

(71) Applicants: Saudi Arabian Oil Company, Dhahran (SA); King Fahd University of Petroleum & Minerals, Dhahran (SA)

(72) Inventors: Mohamed Elanany, Ras Tanura (SA); Khalid Majnouni, Dhahran (SA); Rashed Alessa, Alkubar (SA); Abdullah Al-Malki, Dhahran (SA); Mohammed Al-Daous, Dhahran (SA); Hassan Al-Ajwad, Dhahran (SA); Shaikh Asrof Ali, Dhahran (SA); Shadi Adel, Dhahran (SA); Megat Rithauddeen, Dhahran (SA)

(73) Assignees: Saudi Arabian Oil Company, Dhahran (SA); King Fahd University of Petroleum & Minerals, Dhahran (SA)

( * ) Notice: Subject to any disclaimer, the term of this patent is extended or adjusted under 35 U.S.C. 154(b) by 0 days.

(21) Appl. No.: 15/584,382

(22) Filed: May 2, 2017

(65) Prior Publication Data

US 2017/0321050 A1 Nov. 9, 2017

Related U.S. Application Data

(60) Provisional application No. 62/332,771, filed on May 6, 2016.

(51) Int. Cl.
  *C08L 33/24* (2006.01)
  *C08L 33/26* (2006.01)
  (Continued)

(52) U.S. Cl.
  CPC ............ *C08L 33/26* (2013.01); *C07D 403/00* (2013.01); *C08F 220/54* (2013.01); *C08L 33/14* (2013.01);
  (Continued)

(58) Field of Classification Search
  CPC .............................. C08F 220/54; C08F 220/56
  See application file for complete search history.

(56) References Cited

U.S. PATENT DOCUMENTS

| 4,221,888 A | 9/1980 | Kawakami et al. |
| 4,277,580 A | 7/1981 | Allen et al. |

(Continued)

FOREIGN PATENT DOCUMENTS

| CN | 104449600 A | 3/2015 |
| EP | 161882 A2 | 11/1985 |

(Continued)

OTHER PUBLICATIONS

Kono et al. (Biochimica et Biophysica Acta 1416 (1999) 239-250).*

(Continued)

*Primary Examiner* — Vu A Nguyen
(74) *Attorney, Agent, or Firm* — Dinsmore & Shohl LLP

(57) ABSTRACT

Copolymers having General Formula (I):

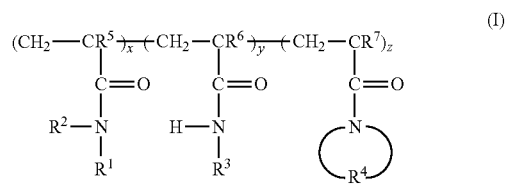

in which $R^1$, $R^2$, and $R^3$ are chosen from $C_1$ to $C_{30}$ aliphatic groups, $R^4$ is chosen from divalent $C_4$ to $C_7$ linear aliphatic (Continued)

groups and divalent $C_4$ to $C_7$ linear heteroaliphatic groups, optionally substituted with one or more $C_1$-$C_6$ linear aliphatic groups, $C_1$-$C_6$ branched aliphatic groups, or combination thereof, $R^5$, $R^6$, and $R^7$ are each independently chosen from methyl or hydrogen, x is chosen from 0 to 0.8, y is chosen from 0 to 0.8, when y is 0, x is greater than 0, and when x is 0, y is greater than 0, and z is chosen from 0.1 to 0.9. The summation of x, y, and z equals 1. Methods for inhibiting formation of clathrate hydrates in a fluid capable of forming the clathrate hydrates, including contacting the fluid with at least one copolymer of General Formula (I).

19 Claims, 13 Drawing Sheets

(51) Int. Cl.
| | |
|---|---|
| *C08F 220/54* | (2006.01) |
| *C08F 220/56* | (2006.01) |
| *C07D 403/00* | (2006.01) |
| *C08L 33/14* | (2006.01) |

(52) U.S. Cl.
CPC ...... *C08L 2205/00* (2013.01); *C09K 2208/22* (2013.01)

(56) References Cited

U.S. PATENT DOCUMENTS

| | | |
|---|---|---|
| 4,363,797 A | 12/1982 | Jacquet et al. |
| 4,435,556 A | 3/1984 | Masler |
| 4,828,710 A | 5/1989 | Itoh et al. |
| 5,413,731 A | 5/1995 | Adler et al. |
| 5,432,292 A | 7/1995 | Sloan, Jr. et al. |
| 5,841,010 A | 11/1998 | Rabeony et al. |
| 6,015,929 A | 1/2000 | Rabeony et al. |
| 6,232,273 B1 | 5/2001 | Namba et al. |
| 6,593,408 B1 | 7/2003 | Takaki et al. |
| 7,183,240 B2 | 2/2007 | Dahlmann et al. |
| 7,214,814 B2 | 5/2007 | Dahlmann et al. |
| 7,297,823 B2 | 11/2007 | Dahlmann et al. |
| 7,381,689 B2 | 6/2008 | Panchalingam et al. |
| 7,662,970 B2 | 2/2010 | Rivers et al. |
| 7,837,746 B2 | 11/2010 | Rivers et al. |
| 7,893,009 B2 | 2/2011 | Leinweber et al. |
| 7,968,500 B2 | 6/2011 | Pakulski et al. |
| 8,034,748 B2 | 10/2011 | Dahlmann et al. |
| 9,145,465 B2 | 9/2015 | Spencer et al. |
| 2004/0024152 A1 | 2/2004 | Toyama et al. |
| 2006/0025603 A1 | 2/2006 | Quinlin et al. |
| 2006/0205603 A1 | 9/2006 | Colle et al. |
| 2008/0177103 A1 | 7/2008 | Leinweber et al. |
| 2008/0221271 A1 | 9/2008 | Duggal et al. |
| 2010/0209476 A1 | 8/2010 | Lim et al. |
| 2011/0152130 A1 | 6/2011 | Adidharma et al. |
| 2012/0080643 A1 | 4/2012 | Leinweber et al. |
| 2013/0098623 A1 | 4/2013 | Spencer et al. |
| 2013/0261275 A1 | 10/2013 | Musa et al. |
| 2014/0148337 A1 | 5/2014 | Schnabel et al. |
| 2015/0322330 A1 | 11/2015 | Spencer et al. |

FOREIGN PATENT DOCUMENTS

| | | |
|---|---|---|
| EP | 163404 A2 | 12/1985 |
| EP | 256797 A1 | 2/1988 |
| GB | 2301825 A | 12/1996 |
| JP | 3851682 B2 | 11/2006 |
| WO | 9325798 A1 | 12/1993 |
| WO | 9608672 A1 | 3/1996 |
| WO | 9641785 A1 | 12/1996 |
| WO | 9819980 A1 | 5/1998 |

OTHER PUBLICATIONS

Skrabania et al. (Langmuir 2007, 23, 84-93).*
Yoshida et al., J. Biomater. Sci. Polymer Edn. 1994, 6(6), 585-598.*
Yoshino et al., Bioconjugate Chem. 2004, 15, 1102-1109.*
International Search Report and Written Opinion dated Sep. 19, 2017 pertaining to International Application No. PCT/US2017030373.
International Search Report and Written Opinion dated Aug. 6, 2017 for PCT/US2017/029283 Filed May 30, 2017. pp. 1-18.
International Search Report and Written Opinion dated Jul. 12, 2017 for PCT/US2017/030795 dated Jul. 30, 2017. pp. 1-10.
International Search Report and Written Opinion dated Jul. 27, 2017 for PCT/US2017/030794 Filed Jul. 20, 2017. pp. 1-9.
"Design, Synthesis, and Aqueous Aggregation Behavior of Nonionic Single and Multiple Thermoresponsive Polymers", Katja Skrabania, et al., Langmuir 2007, vol. 23, Jan. 1, 2007, pp. 84-93.
"Temperature Sensitization of Liposomes by Use of N-Isopropylacrylamide Copolymers with Varying Transition Endotherms", Keisuke Yoshino, et al., Bioconjugate Chem. 2004, Sep. 1, 2004, pp. 1102-1109.
"Thermosensitive polymer-modified liposomes that release contents around physiological temperature", Kenji Kono, et al., Biochimica et Biophysica Acta, Jan. 1, 1999, pp. 239-250.
"Poly(glycidyl methacrylate): a highly versatile polymeric building block for post-polymerization modifications", Polym. Chem., 2013, 4, 124.
Election/Restriction dated Oct. 26, 2017 for U.S. Appl. No. 15/584,389, filed May 2, 2017.
Office Action dated Mar. 9, 2018 pertaining to U.S. Appl. No. 15/584,389.
Election Restriction pertaining to U.S. Appl. No. 15/585,558 dated May 17, 2018.
Election/Restriction Requirement dated Jul. 20, 2018 pertaining to U.S. Appl. No. 15/585,574.
Office Action dated Aug. 1, 2018 pertaining to U.S. Appl. No. 15/585,558.
Arabiyah & Hasbah Offshore & Onshore Facilities, Loss Prevention Plan for Fabrication Activities at Karimun Fabrication Yard, 2012, Saudi Aramco.
Office Action pertaining to U.S. Appl. No. 15/585,574 dated Sep. 27, 2018.
International Preliminary Report on Patentability pertaining to PCT/US2017/030795 dated Nov. 6, 2018.
International Preliminary Report on Patentability pertaining to PCT/US2017/030794 dated Nov. 6, 2018.
International Preliminary Report on Patentability pertaining to PCT/US2017/030373 dated Nov. 6, 2018.

* cited by examiner

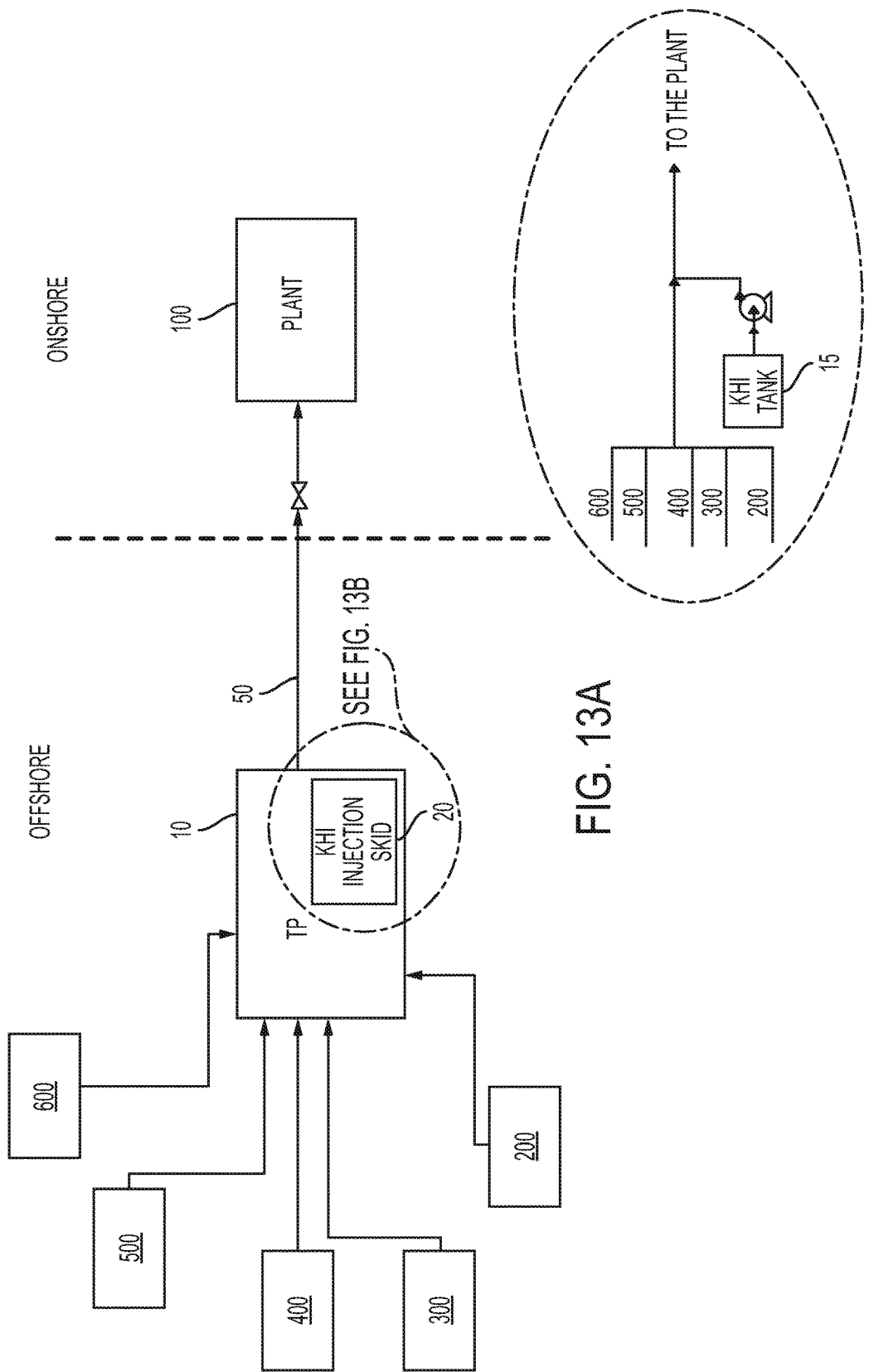

ACRYLAMIDE-BASED COPOLYMERS, TERPOLYMERS, AND USE AS HYDRATE INHIBITORS

CROSS REFERENCE TO RELATED APPLICATIONS

This application claims priority to U.S. Provisional Application No. 62/332,771, filed May 6, 2016, which is incorporated by reference in its entirety.

TECHNICAL FIELD

The present disclosure generally relates to acrylamide-based copolymers and terpolymers, to methods for synthesizing copolymers and terpolymers, and to methods for inhibiting formation of clathrate hydrates.

BACKGROUND

Conditions favoring formation of clathrate hydrates are often found in pipelines. With the expansion of offshore gas exploration and production, the formation of clathrate hydrate formation has become a serious operational concern in both gas transportation and gas processing. Agglomeration and adherence of clathrate hydrates to pipeline walls can reduce gas production, plug sections of the pipeline, and even block the pipeline, leading to a pipeline shutdown. In order to maintain gas production and avoid pipeline shutdown, clathrate hydrate inhibitors have been added to pipeline fluids.

Commercially available clathrate hydrate inhibitors include thermodynamic hydrate inhibitors (that is, THIs), which act to modify the conditions at which clathrate hydrates form in pipeline fluids. For example, THIs may be added to pipeline fluids at high concentrations (for example, up to 0.6 weight/weight, that is w/w of the water cut) to modify the pressure, temperature, or a combination of the pressure and temperature at which clathrate hydrates form. Ethylene glycol (that is, monoethylene glycol or MEG) and methanol are examples of THIs. Another type of commercially available clathrate hydrate inhibitors are low dose hydrate inhibitors (that is, LDHIs), which act to: (1) kinetically delay clathrate hydrate nucleation, and (2) inhibit clathrate hydrate agglomeration. With regard to kinetically delaying clathrate hydrate nucleation, LDHIs may interact with clathrate hydrate nuclei during early formation of clathrate hydrates. With regard to inhibiting clathrate hydrate agglomeration, LDHIs may inhibit clathrate hydrate agglomeration by adsorbing to clathrate hydrates to prevent massive accumulation of clathrate hydrates. In one or more embodiments, LDHIs may inhibit clathrate hydrate agglomeration such that clathrate hydrates are kept in the form of a suspension.

Recently, THIs have been replaced by commercially available LDHIs because THIs are viewed as being difficult to separate from pipeline fluids and harmful to the environment. However, commercially available LDHIs are also imperfect in that some are inefficient or incompatible with other additives, for example, corrosion inhibitors. Further, commercially available LDHIs which are capable of inhibiting clathrate hydrates having a structure (Type) I (that is, SI) crystalline structure under severe conditions, for example, extreme subcooling temperatures and pressure, are limited. Moreover, commercially available LDHIs which are capable of inhibiting clathrate hydrates having a SI crystalline structure are limited to a narrow subcooling temperature range.

SUMMARY

In view of the Background, there is an ongoing need for clathrate hydrate inhibitors and for methods of inhibiting clathrate hydrate formation. Embodiments of the present disclosure are directed to copolymers and terpolymers having General Formula (I):

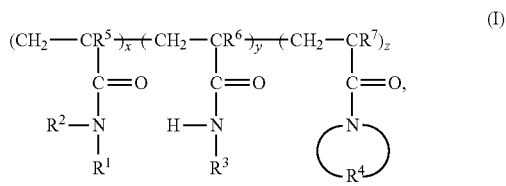

in which: $R^1$, $R^2$, and $R^3$ are each independently chosen from $C_1$ to $C_{30}$ aliphatic groups; $R^4$ is chosen from divalent $C_4$ to $C_7$ linear aliphatic groups and divalent $C_4$ to $C_7$ linear heteroaliphatic groups, optionally substituted with one or more $C_1$-$C_6$ linear aliphatic groups, $C_1$-$C_6$ branched aliphatic groups, or combination thereof, where the divalent $C_4$ to $C_7$ linear heteroaliphatic groups include 1 or 2 heteroatoms independently chosen from O, N, and S; $R^5$, $R^6$, and $R^7$ are each independently chosen from methyl or hydrogen; x is a molar fraction range chosen from 0 to 0.8; y is a molar fraction range chosen from 0 to 0.8, where when y is a molar fraction of 0, x is a molar fraction of greater than 0, and where when x is a molar fraction of 0, y is a molar fraction of greater than 0; and z is a molar fraction range chosen from 0.1 to 0.9, where the summation of x, y, and z equals 1.

Embodiments of the present disclosure are also directed to methods for inhibiting formation of clathrate hydrates in a fluid capable of forming the clathrate hydrates. The methods include contacting the fluid with at least one copolymer or terpolymer of General Formula (I) under conditions suitable for forming the clathrate hydrates:

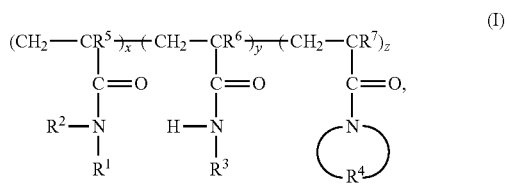

in which: $R^1$, $R^2$, and $R^3$ are each independently chosen from $C_1$ to $C_{30}$ aliphatic groups; $R^4$ is chosen from divalent $C_4$ to $C_7$ linear aliphatic groups and divalent $C_4$ to $C_7$ linear heteroaliphatic groups, optionally substituted with one or more $C_1$-$C_6$ linear aliphatic groups, $C_1$-$C_6$ branched aliphatic groups, or combination thereof, where the divalent $C_4$ to $C_7$ linear heteroaliphatic groups include 1 or 2 heteroatoms independently chosen from O, N, and S; $R^5$, $R^6$, and $R^7$ are each independently chosen from methyl or hydrogen; x is a molar fraction range chosen from 0 to 0.8; y is a molar fraction range chosen from 0 to 0.8, where when y is a molar fraction of 0, x is a molar fraction of greater than 0, and where when x is a molar fraction of 0, y is a molar fraction of greater than 0; and z is a molar fraction range chosen from 0.1 to 0.9, where the summation of x, y, and z equals 1.

Additional features and advantages of the described embodiments in this disclosure will be set forth in the Detailed Description which follows, and in part will be readily apparent to those skilled in the art from that description or recognized by practicing the embodiments described in this disclosure, including the Detailed Description which follows, the claims, as well as the appended drawings.

It is to be understood that both the foregoing general description and the following Detailed Description describe various embodiments and are intended to provide an overview or framework for understanding the nature and character of the claimed subject matter. The accompanying drawings are included to provide a further understanding of the various embodiments, and are incorporated into and constitute a part of this disclosure. The drawings illustrate the various embodiments described in this disclosure, and together with the Detailed Description serve to explain the principles and operations of the claimed subject matter.

BRIEF DESCRIPTION OF THE DRAWINGS

FIG. 13A is a schematic depicting an offshore tie-in-platform in fluidic communication with wellheads and with an onshore plant via pipelines, where the tie-in-platform includes a receptacle for holding clathrate hydrate inhibitors; and FIG. 13B is a schematic depicting the receptacle for holding clathrate hydrate inhibitors of FIG. 13A in fluidic communication with wellheads and with an onshore plant via pipelines.

DETAILED DESCRIPTION

Figure 1:
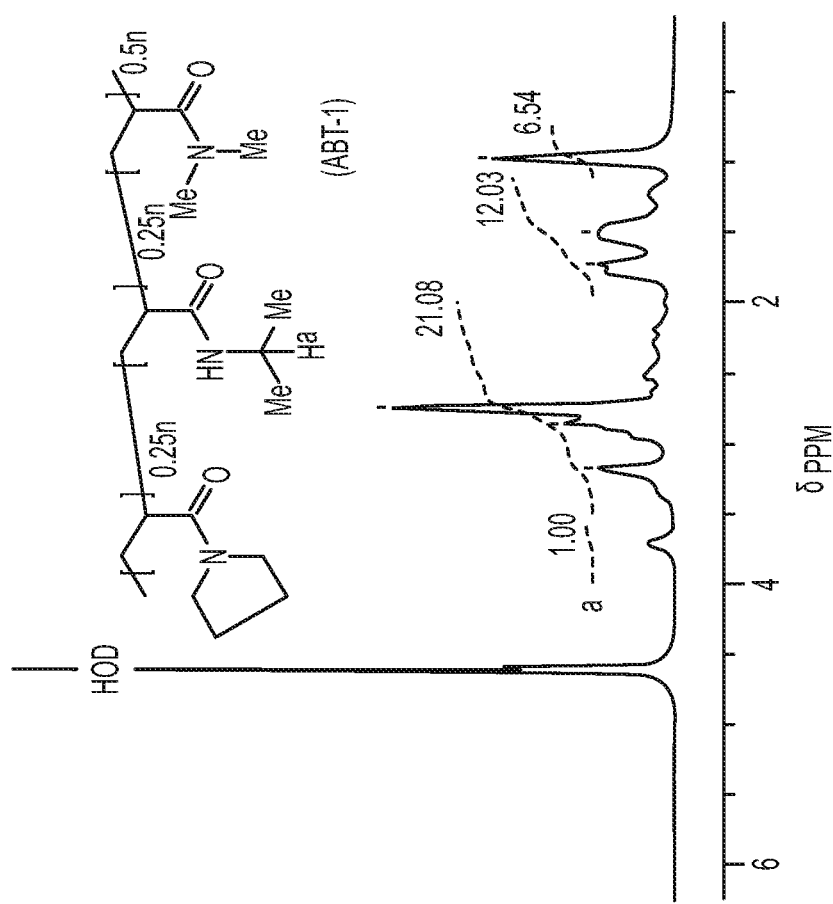
FIG. 1 is a proton nuclear magnetic resonance (that is, $^1$H NMR) spectrum of acrylamide-based terpolymers having structure (ABT-1) as disclosed in Table 1, where the area (a) of 1.00 units belongs to the hydrogen atom marked H$^a$ of monomeric repeating unit structure (M3), where the area of 9.00 units under Chemical Shift δ [parts per million, that is PPM]=0.9-3.5 belongs to the remaining non-exchangeable 9 hydrogen atoms of monomeric repeating unit structure (M3), where the area of 11.0 units belongs to the 11 hydrogen atoms of monomeric repeating unit structure (M1), where the area of 19.65 units belongs to the 9 hydrogen atoms of monomeric repeating unit structure (M2), and where dashed lines are depicted for estimating via integration the number of protons associated with spectrum peaks.

While the following terms are believed to be well understood by one of ordinary skill in the art, definitions are set forth to facilitate explanation of the present-disclosed subject matter.

The term "copolymer" refers to a polymer having two or more different monomeric repeating units. For example, the copolymer may include two different monomeric repeating units (that is, a bipolymer). Alternatively, the copolymer may include three different monomeric repeating units (that is, a terpolymer). In one or more embodiments, the copolymers are random. As will be appreciated by one of ordinary skill in the art, the copolymers are random when the distribution of monomeric repeating units follows statistical laws. For example, copolymers are random when the probability of finding a given monomeric repeating unit at a particular point in the polymer chain is equal to the mole fraction of that monomeric repeating unit in the chain. Random copolymers may also be referred to as statistical copolymers.

The term "aliphatic" refers to both saturated and unsaturated straight chain (that is, unbranched) and branched hydrocarbon radicals. In embodiments, the aliphatic hydrocarbon radicals are monovalent or divalent. As will be appreciated by one of ordinary skill in the art, aliphatic is intended to include, but is not limited to, alkyl, alkenyl, and alkynyl moieties. Thus, the term "alkyl" includes straight and branched alkyl groups. An analogous convention applies to other generic terms such as "alkenyl", "alkynyl" and the like. In certain embodiments, the term "lower alkyl" may be used to indicate alkyl groups (branched or unbranched) having from 1 to 6 carbon atoms.

In embodiments, the alkyl, alkenyl, and alkynyl groups described contain from 1 to 30 aliphatic carbon atoms. In other embodiments, the alkyl, alkenyl, and alkynyl groups described contain from 1 to 20 aliphatic carbon atoms. In still other embodiments, the alkyl, alkenyl, and alkynyl groups described contain from 1 to 8 aliphatic carbon atoms. In yet still other embodiments, the alkyl, alkenyl, and alkynyl groups described contain from 1 to 6 aliphatic carbon atoms. In other embodiments, the alkyl, alkenyl, and alkynyl groups described contain from 1 to 4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "monovalent" refers to a radical having an unsatisfied valence of one, where a valence "-" is unsatisfied at one end of the radical. For example, in embodiments where a hydrocarbon group is present at one end of an aliphatic radical or a heteroaliphatic radical, the aliphatic radical or the heteroaliphatic radical is monovalent when one hydrogen atom has been removed from the hydrocarbon group present at one end of the aliphatic radical or the heteroaliphatic radical. As another example, in embodiments where a heteroatom is present at one end of the heteroaliphatic radical, the heteroaliphatic radical is monovalent when the heteroatoms present at one end of the heteroaliphatic radical has an unsatisfied valence "-".

The term "divalent" refers to a radical having an unsatisfied valence of two, where a valence "-" is unsatisfied at two ends of the radical. For example, in embodiments where a hydrocarbon group is present at two ends of an aliphatic radical or a heteroaliphatic radical, the aliphatic radical or the heteroaliphatic radical is divalent when one hydrogen atom has been removed from each of the hydrocarbon groups present at two ends of the aliphatic radical or the heteroaliphatic radical. As another example, in embodiments where a heteroatom is present at two ends of the heteroaliphatic radical, the heteroaliphatic radical is divalent when each of the heteroatoms present at two ends of the heteroaliphatic radical has an unsatisfied valence "-" Similarly, as another example, in embodiments where a hydrocarbon group is present at one end of a heteroaliphatic radical and a heteroatom is present at one end of the heteroaliphatic radical, the heteroaliphatic radical is divalent when one hydrogen atom has been removed from the hydrocarbon group present at one end of the heteroaliphatic radical and when the heteroatom present at one end of the heteroaliphatic radical has an unsatisfied valence "-".

The term "heteroaliphatic" refers to aliphatic radicals in which one or more carbon atoms in the main chain have been substituted with a heteroatom. By way of example, an aliphatic radical having four main chain atoms where one carbon atom has been substituted with one heteroatom is referred to as a $C_4$ heteroaliphatic. As another example, an aliphatic radical having seven main chain atoms where two carbon atoms have been substituted with two heteroatoms is referred to as a $C_7$ heteroaliphatic. In embodiments, the heteroaliphatic radicals are monovalent or divalent. Thus, heteroaliphatic is intended to include aliphatic chains which contain one or more oxygen, sulfur, or nitrogen atoms, for example, in place of carbon atoms. Heteroaliphatic moieties may be linear or branched, and saturated or unsaturated.

The term "heterocycloalkyl," "heterocycle," or "heterocyclic" refers to radicals that combine the properties of heteroaliphatic and cyclic moieties and include, but are not limited to, saturated and unsaturated mono- or polycyclic ring systems having from 5 to 8 atoms, where at least one ring atom is a N heteroatom; and where zero, one or two ring atoms are additional heteroatoms independently chosen from S, O, and N (where the nitrogen and sulfur heteroatoms may optionally be oxidized). In certain embodiments, the terms heterocycloalkyl, heterocycle or heterocyclic refer to non-aromatic 5-membered, 6-membered, or 7-membered rings or polycyclic moieties where at least one ring atom is a N heteroatom, and where zero, one or two ring atoms are additional heteroatoms independently chosen from S, O, and N (where the nitrogen and sulfur heteroatoms may optionally be oxidized and the nitrogen atom may be quarternized) including, but not limited to, bicyclic or tricyclic groups. Representative heterocycles include, but are not limited to, heterocycles such as pyrrolidinyl, pyrazolinyl, pyrazolidinyl, imidazolidinyl, piperidinyl, piperazinyl, oxazolidinyl, isoxazolidinyl, morpholinyl, thiazolidinyl, isothiazolidinyl, dithiazolyl, dithiazolidinyl, and azepanyl. In embodiments, the heterocycloalkyls, heterocycles or heterocyclics are saturated or unsaturated mono- or polycyclic moieties having from 5 to 8 ring atoms of which one ring atom is N; and of which zero, one or two ring atoms are additional heteroatoms independently chosen from S, O, and N; and the remaining ring atoms are carbon, the radicals being joined to the rest of the molecule via a N ring atom, such as, for example, pyrollidinyl, pyrazolidinyl, imidazolidinyl, piperidinyl, piperazinyl, morpholinyl, thiazolidinyl, and azepanyl.

The term "clathrate hydrates" refers to crystalline water-based solids in which host water molecules enclathrate gas guest molecules. The term "enclathrate" refers to hydrogen bonding of host water molecules around gas guest molecules. In one or more embodiments, crystalline water-based solids in which host water molecules are hydrogen bonded around the gas guest molecules such that the gas guest molecules are trapped inside cages of hydrogen bonded host water molecules. The clathrate hydrates may include a structure (Type) I (that is, SI), a structure (Type) II (that is, SII), or a structure (Type) H (that is, SH) crystalline structure.

The terms "inhibit", "inhibition", and "inhibiting" refer to any improvement in controlling, delaying, reducing, mitigating, preventing, or combination thereof the formation, growth, adherence, agglomeration, or combination thereof of clathrate hydrates in any manner. For example, clathrate hydrate inhibition includes, but should not be limited to, thermodynamically modifying the conditions at which clathrate hydrates form, kinetically delaying clathrate hydrate nucleation, dissolving clathrate hydrates, breaking up clathrate hydrates, or combination thereof. Further, clathrate hydrate inhibition may include the complete cessation of clathrate hydrate formation, where clathrate hydrate formation is entirely prevented.

The terms "formation", "forming", and "form" refer to any process in which host water molecules enclathrate gas guest molecules in a crystalline structure, in which clathrate hydrates grow, in which clathrate hydrates adhere, in which clathrate hydrates agglomerate, or combination thereof.

The terms "subcooling temperature" and "$T_{sc}$" refer to the difference between an operating temperature of a field gas and the three-phase equilibrium temperature of the clathrate hydrate of the field gas at 140 bars. Thus, the term "first subcooling temperature" refers to the difference between an operating temperature of a field gas in a first operation stage and the three-phase equilibrium temperature. In embodiments, the first subcooling temperature is from about 0° C. to about 4.0° C., or from about 0° C. to about 1.0° C., or from about 1.0° C. to about 2.0° C., or from about 2.0° C. to about 3.5° C., or about 4.0° C. Similarly, the term "second subcooling temperature" refers to the difference between an operating temperature of a field gas in a second operation stage and the three-phase equilibrium temperature. In embodiments, the second subcooling temperature is from about 4.0° C. to about 5.6° C., or from about 4.0° C. to about 4.6° C., or from about 4.6° C. to about 5.0° C., or from about 5.0° C. to about 5.6° C., or about 5.6° C. Additionally, the term "third subcooling temperature" refers to the difference between an operating temperature of a field gas in a third operation stage and the three-phase equilibrium temperature. In embodiments, the third subcooling temperature is from about 5.6° C. to about 10.5° C., or from about 5.6° C. to about 7.0° C., or from about 7.0° C. to about 8.6° C., or from about 8.6° C. to about 10.0° C., or about 10.5° C.

Embodiments of the present disclosure are directed toward acrylamide-based copolymers (that is, ABC) having General Formula (I), to methods for synthesizing acrylamide-based copolymers having General Formula (I), and to methods for inhibiting formation of clathrate hydrates using acrylamide-based copolymers having General Formula (I). Embodiments of the acrylamide-based copolymers having General Formula (I) will now be described in detail. Thereafter, embodiments of methods for synthesizing copolymers of General Formula (I) will be described. Then, methods for inhibiting formation of clathrate hydrates using acrylamide-based copolymers having General Formula (I) will be described with reference to FIGS. 13A-13B.

I. Acrylamide-Based Copolymers of General Formula (I)

In embodiments, the disclosure describes acrylamide-based copolymers having General Formula (I):

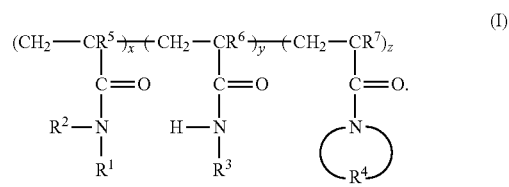

In the copolymers of General Formula (I), $R^1$, $R^2$, and $R^3$ are each independently chosen from $C_1$ to $C_{30}$ saturated aliphatic groups; $R^4$ is chosen from divalent $C_4$ to $C_7$ linear aliphatic groups and divalent $C_4$ to $C_7$ linear heteroaliphatic groups, optionally substituted with one or more $C_1$-$C_6$ linear aliphatic groups, $C_1$-$C_6$ branched aliphatic groups, or combination thereof, where the divalent $C_4$ to $C_7$ linear heteroaliphatic groups include 1 or 2 heteroatoms independently chosen from O, N, and S; $R^5$, $R^6$, and $R^7$ are each independently chosen from methyl or hydrogen; x is a molar fraction range chosen from 0 to about 0.8; y is a molar fraction range chosen from 0 to about 0.8, where when y is a molar fraction of 0, x is a molar fraction of greater than 0, and where when x is a molar fraction of 0, y is a molar fraction of greater than 0; and z is a molar fraction range chosen from about 0.1 to about 0.9, where the summation of x, y, and z equals 1.

In the copolymers of General Formula (I), $R^1$, $R^2$, and $R^3$ are each independently chosen from $C_1$ to $C_{30}$ saturated aliphatic groups. In embodiments, $R^1$, $R^2$, and $R^3$ are each independently chosen from $C_1$ to $C_8$ saturated aliphatic groups. In illustrative, non-limiting embodiments, $R^1$, $R^2$, and $R^3$ are each independently chosen from methyl, ethyl, n-propyl, isopropyl, n-butyl, sec-butyl, isobutyl, tert-butyl, n-pentyl, sec-pentyl, isopentyl, tert-pentyl, n-hexyl, and sec-hexyl. In other illustrative, non-limiting embodiments, $R^1$ is methyl; $R^2$ is methyl; and $R^3$ is isopropyl.

In the copolymers of General Formula (I), $R^4$ is chosen from divalent $C_4$ to $C_7$ linear aliphatic groups and divalent $C_4$ to $C_7$ linear heteroaliphatic groups, where the divalent $C_4$ to $C_7$ linear heteroaliphatic groups include 1 or 2 heteroatoms independently chosen from O, N, and S. The 1 or 2 heteroatoms of the linear heteroaliphatic groups are in addition to the N atom present in the

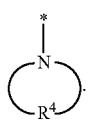

In embodiments, the

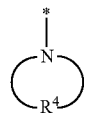

may include up to 3 heteroatoms total, including the N atom present in the

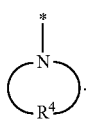

In embodiments, $R^4$ is chosen from divalent $C_4$ to $C_7$ linear aliphatic groups. In further embodiments, $R^4$ is chosen from divalent $C_4$ to $C_6$ linear aliphatic groups.

In one or more embodiments, $R^4$ is optionally substituted with one or more substituting groups. In embodiments where $R^4$ is substituted with one or more substituting groups, $R^4$ may include from 1 to 7, or from 2 to 6, or from 3 to 5 substituting groups. In embodiments where $R^4$ is chosen from divalent $C_4$ to $C_7$ linear aliphatic groups and divalent $C_4$ to $C_7$ linear heteroaliphatic groups and is substituted with one or more substituting groups, the divalent $C_4$ to $C_7$ linear aliphatic groups and divalent $C_4$ to $C_7$ linear heteroaliphatic groups include additional unsatisfied valences "-" within the divalent $C_4$ to $C_7$ linear aliphatic groups and divalent $C_4$ to $C_7$ linear heteroaliphatic groups to accommodate bonding with the substituting groups. For example, in embodiments where $R^4$ is chosen from divalent $C_4$ to $C_7$ linear aliphatic groups and divalent $C_4$ to $C_7$ linear heteroaliphatic groups and is substituted, additional hydrogen atoms may have been removed from the hydrocarbon groups present within the divalent $C_4$ to $C_7$ linear aliphatic groups and divalent $C_4$ to $C_7$ linear heteroaliphatic groups to accommodate bonding with the substituting groups.

In embodiments, $R^4$ is optionally substituted with one or more $C_1$-$C_6$ linear aliphatic groups, $C_1$-$C_6$ branched aliphatic groups, or combination thereof. In illustrative, non-limiting embodiments $R^4$ is substituted with one or more lower alkyls. In other illustrative, non-limiting embodiments, $R^4$ is substituted with one or more $C_1$-$C_3$ linear aliphatic groups, $C_1$-$C_3$ branched aliphatic groups, or combination thereof. In still other illustrative, non-limiting embodiments, $R^4$ is substituted with one or more substituting groups independently chosen from methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties, or combination thereof.

In embodiments where $R^4$ is chosen from the divalent $C_4$ to $C_7$ linear aliphatic groups and the divalent $C_4$ to $C_7$ linear heteroaliphatic groups, the $C_4$ to $C_7$ linear aliphatic groups and the $C_4$ to $C_7$ linear heteroaliphatic groups include an unsatisfied valence "-" at two ends. In this way, $R^4$ forms a heterocycloalkyl or heterocycle when bonded with the —N— in the rest of the copolymer molecule via its two unsatisfied end valences. In embodiments, the heterocycloalkyl or heterocycle formed when $R^4$ is bonded with the —N— in the rest of the copolymer is non-aromatic. In embodiments, the heterocycloalkyl or heterocycle formed when $R^4$ is bonded with the —N— in the rest of the copolymer is partially saturated. In illustrative, non-limiting embodiments, the heterocycloalkyl or heterocycle formed is chosen from pyrollidinyl, pyrazolidinyl, imidazolidinyl, piperidinyl, piperazinyl, morpholinyl, thiazolidinyl, and azepanyl. In further illustrative, non-limiting embodiments, the heterocycloalkyl or heterocycle formed is chosen from pyrrolidinyl and piperidinyl. In embodiments, the heterocycloalkyl or heterocycle formed has the following structure:

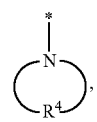

where the heterocycloalkyl or heterocycle is attached to the rest of the copolymer molecule via *. In illustrative, non-limiting embodiments, the

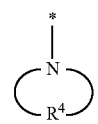

is chosen from

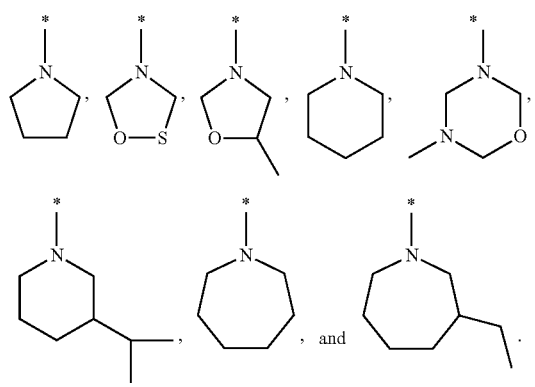

In other illustrative, non-limiting embodiments, the

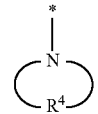

is chosen from

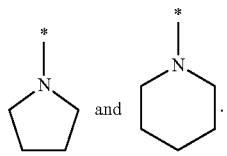

In the copolymers of General Formula (I), $R^5$, $R^6$, and $R^7$ are each independently chosen from methyl or hydrogen. In embodiments, at least one of $R^5$, $R^6$, and $R^7$ is hydrogen. In embodiments, at least one of $R^5$, $R^6$, and $R^7$ is methyl.

In the copolymers of General Formula (I), x is a molar fraction range chosen from 0 to about 0.8. In embodiments, x is a molar fraction range chosen from 0 to about 0.75, or a molar fraction range chosen from 0 to about 0.2, or a molar fraction of about 0.5. In illustrative, non-limiting embodiments, x is a molar fraction range chosen from 0 to about 0.5. In other illustrative, non-limiting embodiments, x is a molar fraction range chosen from about 0.5 to about 0.75. In still other illustrative, non-limiting embodiments, x is a molar fraction of greater than 0. In yet other illustrative non-limiting embodiments, x is a molar fraction of 0.

In the copolymers of General Formula (I), y is a molar fraction range chosen from 0 to about 0.8. In embodiments, y is a molar fraction range chosen from 0 to about 0.75, or a molar fraction range chosen from about 0.1 to about 0.5, or a molar fraction of about 0.25. In illustrative, non-limiting embodiments, y is a molar fraction range chosen from about 0.5 to about 0.75. In other illustrative, non-limiting embodiments, y is a molar fraction range of from 0 to about 0.5. In still other illustrative, non-limiting embodiments, y is a molar fraction of greater than 0. In yet other illustrative, non-limiting embodiments, y is a molar fraction of 0.

In the copolymers of General Formula (I), z is a molar fraction range chosen from about 0.1 to about 0.9. In embodiments, z is a molar fraction range chosen from about 0.1 to about 0.75, or a molar fraction range chosen from about 0.1 to about 0.75, or a molar fraction range chosen from about 0.2 to about 0.25. In illustrative, non-limiting embodiments, z is a molar fraction range chosen from about 0.2 to about 0.75. In other illustrative, non-limiting embodiments, z is a molar fraction range chosen from about 0.1 to about 0.25. In still other illustrative, non-limiting embodiments, z is a molar fraction range chosen from about 0.25 to about 0.5. In yet other illustrative, non-limiting embodiments, z is a molar fraction of greater than 0.

In the copolymers of General Formula (I), the summation of x, y, and z equals 1, provided that z is a molar fraction of greater than 0. Further, in embodiments, while x or y may be a molar fraction of 0, x and y may not each be a molar fraction of 0. Rather, in embodiments when y is a molar fraction of 0, x is a molar fraction of greater than 0. Similarly, in embodiments when x is a molar fraction of 0, y is a molar fraction of greater than 0. In embodiments, y and z are equimolar fractions. In other embodiments, x and z are equimolar fractions.

In embodiments, the viscosity average molecular weight of the copolymers of General Formula (I) is from about 1,000 grams/mole, that is g/mol, to about 1,000,000 g/mol, or from about 1,500 g/mol to about 100,000 g/mol, or from about 5,000 g/mol to about 50,000 g/mol, or about 20,000 g/mol. In illustrative, non-limiting embodiments, the viscosity average molecular weight of the copolymers of General Formula (I) is from about 1,500 g/mol to about 20,000 g/mol. In embodiments, the viscosity average molecular weight of the copolymers was determined via gel permeation chromatography (that is, GPC), employing 0.7% triethylamine in tetrahydrofuran (that is, THF) as a mobile phase, Phenogel™ (Phenomenex, Sutter Creek, Calif.) as stationary phases (of differing pore sizes, 500 Å, 100 Å, and 50 Å) in three columns in series, with a refractive index detector (that is, RID). Calibration was performed using polystyrene standards. Moreover, the viscosity average molecular weight of the copolymers of General Formula (I) as determined by GPC was confirmed via sulfur elemental analysis.

In illustrative, non-limiting embodiments, $R^1$, $R^2$, and $R^3$ are each independently chosen from $C_1$ to $C_8$ saturated aliphatic groups; $R^4$ is chosen from divalent $C_4$ to $C_7$ linear aliphatic groups; x is a molar fraction range chosen from 0 to about 0.5; y is a molar fraction range chosen from 0 to about 0.5; and z is a molar fraction range chosen from about 0.2 to about 0.75. In other illustrative, non-limiting embodiments, $R^1$, $R^2$, and $R^3$ are each independently chosen from methyl, ethyl, n-propyl, isopropyl, n-butyl, sec-butyl, isobutyl, tert-butyl, n-pentyl, sec-pentyl, isopentyl, tert-pentyl, n-hexyl, and sec-hexyl; $R^4$ is chosen from divalent $C_4$ to $C_6$ linear aliphatic groups; x is a molar fraction range chosen from 0 to about 0.2; y is a molar fraction range chosen from 0 to about 0.5; and z is a molar fraction range chosen from 0.2 to about 0.75. In still other illustrative, non-limiting embodiments,

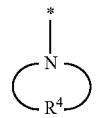

is chosen from

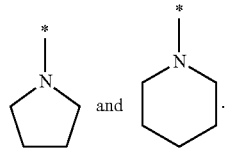

In yet still other illustrative, non-limiting embodiments, $R^1$ is methyl; $R^2$ is methyl; $R^3$ is isopropyl; x is a molar fraction range chosen from about 0.5 to about 0.75; y is a molar fraction range chosen from about 0.1 to about 0.25; and z is a molar fraction range chosen from about 0.1 to about 0.25.

In still other illustrative, non-limiting embodiments, x is a molar fraction of greater than 0; y is a molar fraction of greater than 0; and y and z are equimolar fractions. In other illustrative, non-limiting embodiments, y is a molar fraction of 0; x is a molar fraction range chosen from about 0.5 to about 0.75; and z is a molar fraction range chosen from about 0.25 to about 0.5. In yet other illustrative, non-limiting embodiments, y is a molar fraction of 0; and x and z are equimolar fractions. In still other illustrative, non-limiting embodiments, x is a molar fraction of 0; y is a molar fraction range chosen from about 0.5 to about 0.75; and z is a molar fraction range chosen from about 0.25 to about 0.5. In yet other illustrative, non-limiting embodiments, x is a molar fraction of 0; and y and z are equimolar fractions.

In Table 1, copolymers having General Formula (I) according to various embodiments are provided:

TABLE 1

Copolymers of General Formula (I)

| Reference | Copolymer of General Formula (I) |
|---|---|
| ABT-1 | 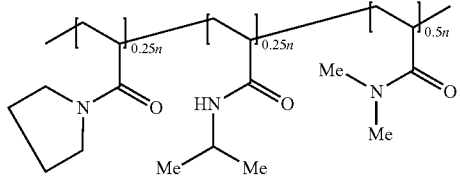 |
| ABT-2 | 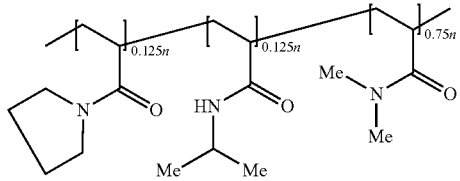 |
| ABC-3 | 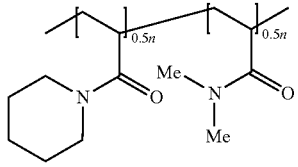 |
| ABC-4 | 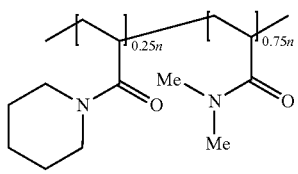 |
| ABC-5 | 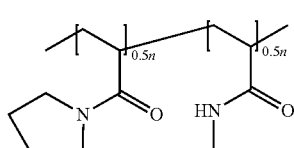 |
| ABT-6 | 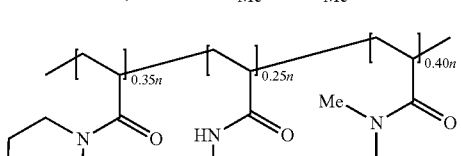 |
| ABT-7 | 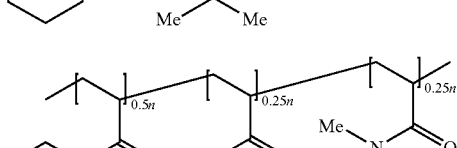 |
| ABC-8 | 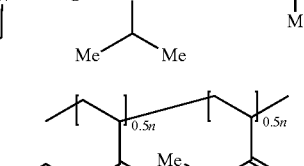 |

Embodiments of acrylamide-based copolymers having General Formula (I) have been described in detail. Embodiments of methods for synthesizing the copolymers of General Formula (I) will be described.

II. Methods for Synthesizing the Copolymers of General Formula (I)

In embodiments, the disclosure describes methods for synthesizing the copolymers of General Formula (I). However, the copolymers of General Formula (I) may be synthesized via any suitable synthetic scheme known to a person of ordinary skill in the art. In illustrative, non-limiting embodiments, the methods for synthesizing the copolymers of General Formula (I) include providing 4,4'-Azobis(4-cyanovaleric acid) (that is, ABCVA) (about 350 milligrams, that is mg, 1.25 millimole, that is mmol) with a solution having monomeric repeating units having formula (1a) (about 18 mmol), (1b) (about 36 mmol) and (1c) (about 18 mmol):

(1a)

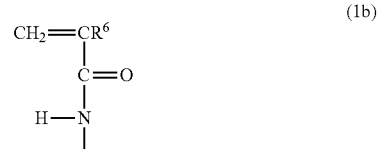

(1b)

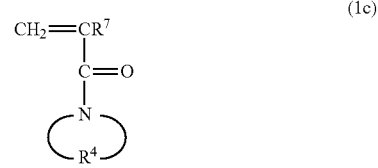

(1c)

and thioglycolic acid (about 334 mg, 3.60 mmol) in water (about 42 milliliters, that is mL) under $N_2$ to form a reaction mixture.

In embodiments, the reaction mixture is stirred under $N_2$ at about 63° C. using a magnetic stir-bar for 24 hours to obtain a reaction product including a synthesized acrylamide-based terpolymer. After 24 hours, in embodiments, the reaction product is homogenous, cooled to room temperature, washed with petroleum ether (about 3×20 mL), and freeze-dried. In some embodiments, a cloudy suspension may be observed after stirring for a few hours under $N_2$ at about 63° C. However, in embodiments, the cloudy suspension disappears upon cooling to room temperature.

In embodiments, $R^1$, $R^2$, $R^3$, $R^4$, $R^5$, $R^6$, and $R^7$ of monomeric repeating units having formula (1a), (1b), and (1c) are as described previously with regard to General Formula (I). As will be appreciated by one of ordinary skill in the art, quantities of reactants, for example, monomeric repeating units (1a), (1b), and (1c), in the solution may be adjusted to achieve varying molar fractions x, y, or z, of each monomeric repeating unit. Further, as will also be appreciated by one of ordinary skill in the art, bipolymers and terpolymers may be synthesized via the methods described in this disclosure by adding only the monomeric repeating units (1a), (1b), and (1c) which are desired in the copolymers of General Formula (I).

Embodiments of methods for synthesizing the copolymers of General Formula (I) have now been described in detail. Embodiments of methods for inhibiting formation of clathrate hydrates will now be described in detail with reference to FIGS. 13A-13B.

III. Methods for Inhibiting Formation of Clathrate Hydrates

In one or more embodiments, the disclosure describes methods for inhibiting clathrate hydrates in a fluid capable of forming the clathrate hydrates, the methods including contacting the fluid with at least one copolymer of General Formula (I) under conditions suitable for forming the clathrate hydrates. In further embodiments, the at least one copolymer of General Formula (I) is as described previously.

In embodiments, in the at least one copolymer of General Formula (I), $R^1$, $R^2$, and $R^3$ are each independently chosen from $C_1$ to $C_{30}$ saturated aliphatic groups; $R^4$ is chosen from divalent $C_4$ to $C_7$ linear aliphatic groups and divalent $C_4$ to $C_7$ linear heteroaliphatic groups, optionally substituted with one or more $C_1$-$C_6$ linear aliphatic groups, $C_1$-$C_6$ branched aliphatic groups, or combination thereof, where the divalent $C_4$ to $C_7$ linear heteroaliphatic groups include 1 or 2 heteroatoms independently chosen from O, N, and S; $R^5$, $R^6$, and $R^7$ are each independently chosen from methyl or hydrogen; x is a molar fraction range chosen from 0 to about 0.8; y is a molar fraction range chosen from 0 to about 0.8, where when y is a molar fraction of 0, x is a molar fraction of greater than 0, and where when x is a molar fraction of 0, y is a molar fraction of greater than 0; and z is a molar fraction range chosen from about 0.1 to about 0.9, where the summation of x, y, and z equals 1. In embodiments, the fluid is contacted with the at least one copolymer of General Formula (I) and with at least one of a corrosion inhibitor or a solvent.

In illustrative, non-limiting embodiments, in the at least one copolymer of General Formula (I), $R^1$, $R^2$, and $R^3$ are each independently chosen from $C_1$ to $C_8$ saturated aliphatic groups; $R^4$ is chosen from divalent $C_4$ to $C_7$ linear aliphatic groups; x is a molar fraction range chosen from 0 to about 0.5; y is a molar fraction range chosen from 0 to about 0.5; and z is a molar fraction range chosen from about 0.2 to about 0.75. In other illustrative, non-limiting embodiments, in the at least one copolymer of General Formula (I), $R^1$, $R^2$, and $R^3$ are each independently chosen from $C_1$ to $C_8$ saturated aliphatic groups; $R^4$ is chosen from divalent $C_4$ to $C_7$ linear aliphatic groups; x is a molar fraction of greater than 0; y is a molar fraction of greater than 0; and y and z are equimolar fractions. In still other illustrative, non-limiting embodiments, in the at least one copolymer of General Formula (I),

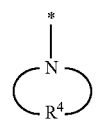

is chosen from and

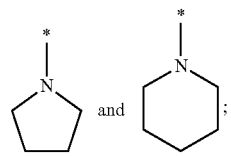

x is a molar fraction range chosen from about 0.5 to about 0.75; y is a molar fraction range chosen from about 0.1 to about 0.25; and z is a molar fraction range chosen from about 0.1 to about 0.25.

In still other illustrative, non-limiting embodiments, in the at least one copolymer of General Formula (I), y is a molar fraction of 0; x is a molar fraction range chosen from about 0.5 to about 0.75; and z is a molar fraction range chosen from about 0.25 to about 0.5. In yet still other illustrative, non-limiting embodiments, in the at least one copolymer of General Formula (I), y is a molar fraction of 0; and x and z are equimolar fractions. In other illustrative, non-limiting embodiments, in the at least one copolymer of General Formula (I), x is a molar fraction of 0; y is a molar fraction range chosen from about 0.5 to about 0.75; and z is a molar fraction range chosen from about 0.25 to about 0.5. In still other illustrative, non-limiting embodiments, in the at least one copolymer of General Formula (I), x is a molar fraction of 0; and y and z are equimolar fractions. In yet other illustrative, non-limiting embodiments, in the at least one copolymer of General Formula (I), the viscosity average molecular weight of the copolymer is from about 1,500 g/mol to about 20,000 g/mol.

In embodiments, the fluid is contacted with a formulation including the at least one copolymer of General Formula (I). In embodiments, the fluid is contacted with about 3 weight % of the formulation, where the amount of formulation relates to the percentage of the water cut. More specifically, in embodiments, the formulation includes one or more of the at least one copolymer of General Formula (I) (for example, two or more copolymers of General Formula (I) could be used), solvents, or additives. In embodiments, the at least one copolymer of General Formula (I) is compatible with additives. In embodiments, the additives are chosen from corrosion inhibitors and synergists. In illustrative, non-limiting embodiments, the formulation includes from about 0.01% to about 15% of the at least one copolymer of General Formula (I), from about 0% to about 20% of the solvent, and from about 0% to about 1% of the additive. In other illustrative, non-limiting embodiments, the formulation includes from about 0.1% to about 5% of the at least one copolymer of General Formula (I), from about 0% to about 20% of the solvent, from about 0% to about 10% of the additives, from 0 parts per million (that is, ppm; a mass fraction) to about 3000 ppm of the corrosion inhibitors, from 0 ppm to about 3000 ppm of the scale inhibitors, from 0% to about 40% of the thermodynamic hydrate inhibitors, and from about 0.1% to about 10% of the anti-agglomerates. In embodiments, the amounts disclosed of the formulation relate to the percentage or ppm of the water cut.

In illustrative, non-limiting embodiments, the solvents are chosen from water, alcohols, for example, monoethylene glycol, methanol, ethanol, and isobutanol, ketones, ethers, and non-polar aromatics, for example, toluene and benzene. In further illustrative, non-limiting embodiments, the solvents are alcohols chosen from glycols, for example, monoethylene glycol. In other illustrative, non-limiting embodiments, the additives are chosen from corrosion inhibitors and synergists. In illustrative, non-limiting embodiments, the corrosion inhibitors include gas corrosion inhibitors. In embodiments, the synergists are chosen from scale inhibitors, thermodynamic hydrate inhibitors, low dose hydrate inhibitors, and anti-agglomerates. In illustrative, non-limiting embodiments, the thermodynamic hydrate inhibitors are chosen from glycol ethers and methanol. In illustrative, non-limiting embodiments, low dose hydrate inhibitors are chosen from Poly(N-vinylcaprolactam) and poly(N-methyl-N-vinylacetamide).

In embodiments, the fluid is contacted with at least one copolymer of General Formula (I) under conditions suitable for forming clathrate hydrates. In embodiments, the at least one copolymer of General Formula (I) is contacted with the fluid via methods known to one of ordinary skill in the art. For example, the at least one copolymer of General Formula (I) may be contacted with the fluid via adding, combining, mixing, injecting, or combination thereof. In illustrative, non-limiting embodiments, conditions suitable for forming clathrate hydrates include conditions where the pressure on the fluid is from about 11 bara to about 200 bara, or from about 11 bara to about 50 bara, or from about 50 bara to about 100 bara, or from about 100 bara to about 150 bara, or from about 150 bara to about 200 bara; and also includes conditions where the temperature of the fluid is from about 0° C. to about 25° C., or from about 0° C. to about 12° C., or from about 12° C. to about 16° C., or from about 16° C. to about 19° C., or from about 19° C. to about 25° C.

In other embodiments, contacting the fluid with at least one copolymer of General Formula (I) under conditions suitable for forming the clathrate hydrates is effective to inhibit or inhibits the formation of the clathrate hydrates at a first subcooling temperature. In other embodiments, contacting the fluid with at least one copolymer of General Formula (I) under conditions suitable for forming the clathrate hydrates is effective to inhibit or inhibits the formation of the clathrate hydrates at a second subcooling temperature. In still other embodiments, contacting the fluid with at least one copolymer of General Formula (I) under conditions suitable for forming the clathrate hydrates is effective to inhibit or inhibits the formation of the clathrate hydrates at a third subcooling temperature.

In illustrative, non-limiting embodiments, contacting the fluid with at least one copolymer of General Formula (I) under conditions suitable for forming the clathrate hydrates is effective to inhibit or inhibits the formation of the clathrate hydrates in a pressure range of from about 40 bars to about 200 bars. In other illustrative, non-limiting embodiments, contacting the fluid with at least one copolymer of General Formula (I) under conditions suitable for forming the clathrate hydrates is effective to inhibit or inhibits the formation of the clathrate hydrates in a pressure range of from about 70 bars to about 100 bars.

In embodiments, the fluid capable of forming clathrate hydrates includes water host molecules and natural gas guest molecules. In further embodiments, the natural gas guest molecules are chosen from methane, ethane, propane, butane, pentane, carbon dioxide, hydrogen sulfide, nitrogen, or combination thereof. In illustrative, non-limiting embodiments, the fluid capable of forming clathrate hydrates includes natural gas guest molecules in the following compositional amounts: methane (from about 60-90 mole %); ethane (from about 0-4 mole %); propane (from about 0-1 mole %); butane (from about 0-1 mole %); carbon dioxide (from about 5-15 mole %); hydrogen sulfide (from about 0-5 mole %); and nitrogen (from about 5-15 mole %). In other embodiments, the fluid capable of forming clathrate hydrates includes brine, such as is described subsequently in Table 2. In illustrative, non-limiting embodiments, the brine includes chloride anions, sodium cations, acetic acid, formic acid, a conjugate base of acetic acid, a conjugate base of formic acid, or combination thereof.

In illustrative, non-limiting embodiments, the fluid capable of forming clathrate hydrates includes acid gas guest molecules. For example, in embodiments, the fluid capable of forming clathrate hydrates includes carbon dioxide and hydrogen sulfide. In illustrative, non-limiting embodiments, the fluid capable of forming clathrate hydrates is rich in carbon dioxide, hydrogen sulfide, or a combination of carbon dioxide and hydrogen sulfide. For example, the fluid capable of forming clathrate hydrates may be rich in hydrogen sulfide where it includes at least about 2 mole % of hydrogen sulfide. As another example, the fluid capable of forming clathrate hydrates may be rich in carbon dioxide where it includes at least about 8 mole % of carbon dioxide. As yet another example, the fluid capable of forming clathrate hydrates may be rich in carbon dioxide and hydrogen sulfide where it includes at least about 8 mole % of carbon dioxide and at least about 2 mole % of hydrogen sulfide. In still other illustrative, non-limiting embodiments, the fluid capable of forming clathrate hydrates includes carbon dioxide, hydrogen sulfide, nitrogen, or combination thereof. In yet other illustrative, non-limiting embodiments, the fluid capable of forming clathrate hydrates includes methane, ethane, propane, butane, carbon dioxide, hydrogen sulfide, and nitrogen gas guest molecules. In yet still other illustrative, non-limiting embodiments, the fluid capable of forming clathrate hydrates does not include hydrogen sulfide, carbon dioxide, or a combination of hydrogen sulfide and carbon dioxide.

In embodiments, the fluid capable of forming clathrate hydrates is capable of forming SI clathrate hydrates, SII clathrate hydrates, or combination thereof. In embodiments, fluids capable of forming SI clathrate hydrates include at least one of methane, ethane, propane, butane, carbon dioxide, or hydrogen sulfide. In other embodiments, fluids capable of forming SII clathrate hydrates include at least one of propane, butane, or pentane. In embodiments, SI clathrate hydrates and SII clathrate hydrates have crystalline cubic structures which are well known to one of ordinary skill in the art. further embodiments where the fluid capable of forming clathrate hydrates is capable of forming SI clathrate hydrates, SII clathrate hydrates, or combination thereof, the contacting is effective to inhibit or inhibits formation of SI clathrate hydrates, SII clathrate hydrates, or combination thereof.

In embodiments, the fluid is contacted with the at least one copolymer of General Formula (I) in an amount effective to inhibit clathrate hydrate formation. In specific embodiments, the fluid is contacted with from about 0.1 weight %, that is wt %, to about 7 wt % of the water cut, or from about 0.3 wt % to about 5 wt % of the water cut, or from about 0.5 wt % to about 3 wt % of the water cut.

As shown in FIGS. 13A-13B, in embodiments, the fluid capable of forming the clathrate hydrates is contacted with the at least one copolymer of General Formula (I) at a tie-in-platform 10. As shown in FIGS. 13A-13B, in embodiments, the tie-in-platform 10 is an offshore platform which is in fluidic communication with an onshore plant 100 via a pipeline 50. In embodiments, the tie-in-platform 10 is in fluidic communication with wellheads 200, 300, 400, 500, and 600, which provide an interface for drilling and production equipment. In embodiments, the fluid capable of forming the clathrate hydrates is flowing in a pipeline 50. In further embodiments, the fluid capable of forming the clathrate hydrates is flowing in pipeline 50 from an offshore site to an onshore site. In illustrative, non-limiting embodiments, the fluid capable of forming the clathrate hydrates is flowing in pipeline 50 from the tie-in-platform 10 to the onshore plant 100. In illustrative, non-limiting embodiments, the at least one copolymer of General Formula (I) is injected into the fluid capable of forming the clathrate hydrates at the tie-in-platform 10.

In embodiments, the tie-in-platform 10 includes a receptacle 15 for holding clathrate hydrate inhibitors and a clathrate hydrate inhibitor injection skid 20. In illustrative, non-limiting embodiments, the at least one copolymer of General Formula (I) is held in the receptacle 15 for holding clathrate hydrate inhibitors. In illustrative, non-limiting embodiments, the at least one copolymer of General Formula (I) is injected into the fluid capable of forming the clathrate hydrates via the clathrate hydrate inhibitor injection skid 20.

Embodiments of methods for inhibiting formation of clathrate hydrates using the acrylamide-based copolymers having General Formula (I) have been described in detail.

EXAMPLES

The following non-limiting examples illustrate the synthesis of the copolymers having General Formula (I) and of comparative homopolymers, and also illustrate methods of the present disclosure. The compounds synthesized should be understood to be illustrative in nature and in no regard limiting to the scope of General Formula (I) or of the methods described.

Example 1: Synthesis of Acrylamide-Based Terpolymers Having General Formula (I)

Materials and Methods.

Acrylamide-based terpolymers (that is, ABT) having General Formula (I) in which $R^1$ is methyl, $R^2$ is methyl, $R^3$ is isopropyl, $R^4$ is —(CH$_2$)$_4$—, x is 0.25, y is 0.25, and z is 0.5, were synthesized in accordance with the following reaction scheme:

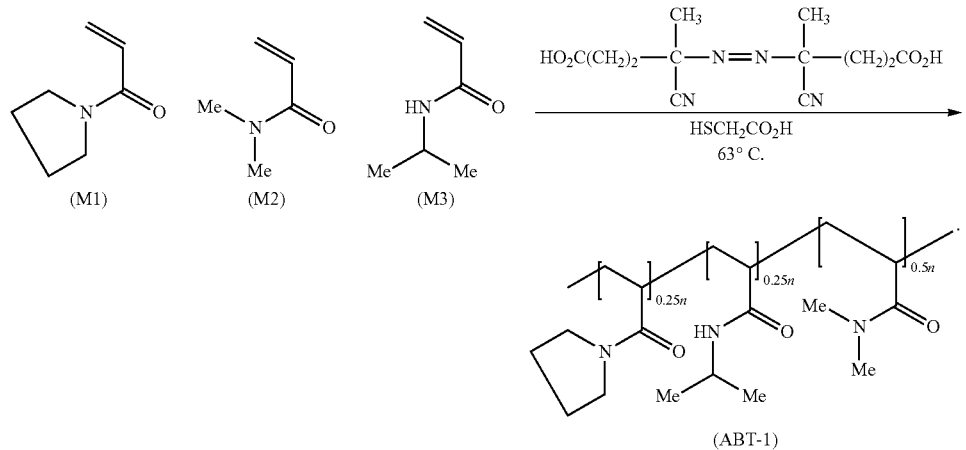

More specifically, acrylamide-based terpolymers having General Formula (I) were synthesized by adding 4,4'-Azobis (4-cyanovaleric acid) (that is, ABCVA) (about 350 mg, 1.25 mmol) to a solution having a monomeric repeating unit of structure (M1) (about 18 mmol):

(M1)

a monomeric repeating unit of structure (M2) (about 36 mmol):

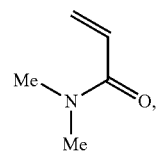

(M2)

a monomeric repeating unit of structure (M3) (about 18 mmol):

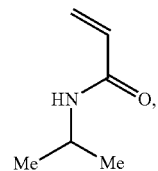

(M3)

and
thioglycolic acid (about 334 mg, 3.60 mmol) in water (about 42 mL) under $N_2$ to form a reaction mixture.

The reaction mixture was stirred under $N_2$ at about 63° C. using a magnetic stir-bar for 24 hours. After 24 hours, the reaction mixture was homogenous and cooled to room temperature. The reaction mixture was then washed with petroleum ether (about 3×20 mL) and freeze-dried to obtain an acrylamide-based terpolymer of structure (ABT-1):

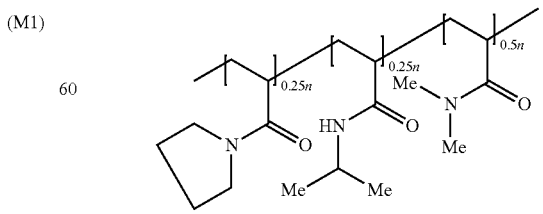

(ABT-1)

as a white polymer (Yield: about 91%).

Results.

The terpolymer of structure (ABT-1) did not show a lower critical solution temperature (that is, LCST) in the range 20° C. to 63° C. The $^1$H NMR spectrum was carefully analyzed to determine that the terpolymer of structure (ABT-1) had a respective terpolymer composition of about 1:1:2. For example, referencing FIG. 1, for a ratio of about 1:1:2, the area (a) of about 1.00 units would belong to the hydrogen atom marked $H^\alpha$ of monomeric repeating unit structure (M3), where the area of about 9.00 units under about δ 0.9-3.5 ppm would belong to the remaining non-exchangeable 9 hydrogen atoms of monomeric repeating unit structure (M3), where the area of about 11.0 units would belong to the 11 hydrogen atoms of monomeric repeating unit structure (M1), and where the area of about 19.65 units would belong to the 9 hydrogen atoms of monomeric repeating unit structure (M2). Because the total area in the range is about 39.65 units (that is, about 21.08+12.03+6.54), after subtracting about 20.00 units for the monomeric repeating unit structures (M1) and (M3), about 19.65 units remain which would belong to the contribution of the 9 hydrogen atoms of monomeric repeating unit structure (M2).

The ratio of the monomeric repeating unit structures (M1):(M3):(M2) for a single hydrogen is thus about 1:1:(19.65/9), that is, about 1.00:1.00:2.18. This is almost identical to the feed ratio of about 1:1:2.

Example 2: Synthesis of Acrylamide-Based Terpolymers Having General Formula (I)

Materials and Methods.

Acrylamide-based terpolymers having General Formula (I) in which $R^1$ is methyl, $R^2$ is methyl, $R^3$ is isopropyl, $R^4$ is —$(CH_2)_4$—, x is 0.125, y is 0.125, and z is 0.75, were synthesized as in Example 1 except as indicated otherwise. More specifically, acrylamide-based terpolymers having General Formula (I) were synthesized by adding ABCVA (about 350 mg, 1.25 mmol) to a solution having a monomeric repeating unit of structure (M1) (about 9 mmol):

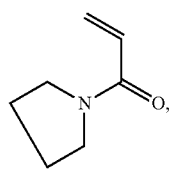
(M1)

a monomeric repeating unit of structure (M2) (about 54 mmol):

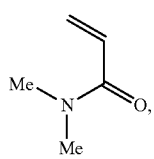
(M2)

a monomeric repeating unit of structure (M3) (about 9 mmol):

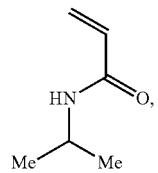
(M3)

and thioglycolic acid (about 334 mg, 3.60 mmol) in water (about 42 mL) under $N_2$ to form a reaction mixture.

The reaction mixture was stirred under $N_2$ at about 63° C. using a magnetic stir-bar for 24 hours. After 24 hours, the reaction mixture was homogenous and cooled to room temperature. The reaction mixture was then washed with petroleum ether (about 3×20 mL) and freeze-dried to obtain an acrylamide-based terpolymer of structure (ABT-2):

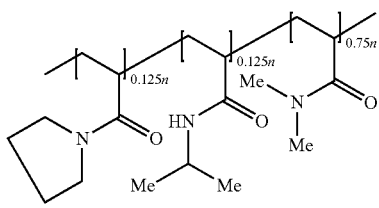
(ABT-2)

as a white polymer (Yield: about 94%).

Results.

Figure 2:
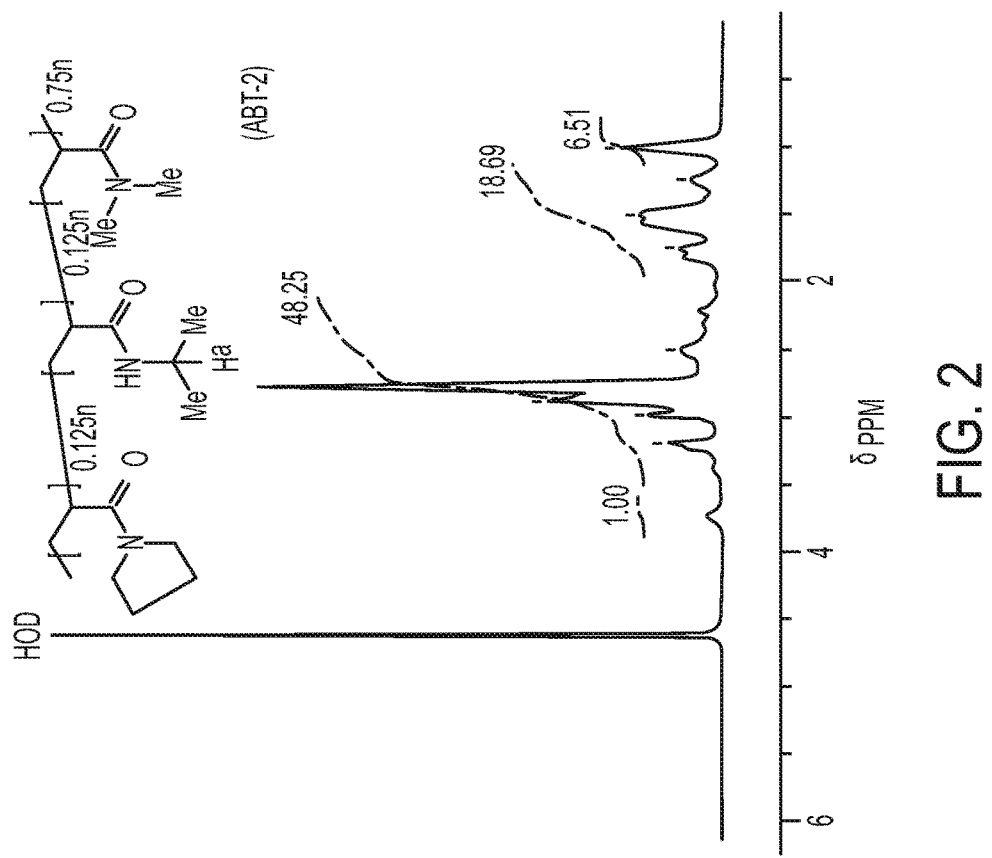
FIG. 2 is a $^1$H NMR spectrum of acrylamide-based terpolymers having structure (ABT-2) as disclosed in Table 1, where the area of 1.00 units belongs to the hydrogen atom marked H$^a$ of monomeric repeating unit structure (M3), where the area of 9.00 units under Chemical Shift δ=0.9-3.5 ppm belongs to the remaining non-exchangeable 9 hydrogen atoms of monomeric repeating unit structure (M3), where the area of 11.0 units belongs to the 11 hydrogen atoms of monomeric repeating unit structure (M1), and where the area of 53.5 units belongs to the 9 hydrogen atoms of the monomeric repeating unit structure (M2)

The terpolymer of structure (ABT-2) did not show a LCST in the range 20° C. to 63° C. The $^1$H NMR spectrum was carefully analyzed to determine that the terpolymer of structure (ABT-2) had a respective polymer composition of about 1:1:6. For example, referencing FIG. 2, for a ratio of about 1:1:6, the area of about 1.00 units would belong to the hydrogen atom marked $H^\alpha$ of monomeric repeating unit structure (M3), where the area of about 9.00 units under about δ 0.9-3.5 ppm would belong to the remaining non-exchangeable 9 hydrogen atoms of monomeric repeating unit structure (M3), where the area of about 11.0 units would belong to the 11 hydrogen atoms of monomeric repeating unit structure (M1), and where the area of about 53.5 units would belong to the 9 hydrogen atoms of the monomeric repeating unit structure (M2). Because the total area in the range is about 73.5 units (that is, about 48.25+18.69+6.51), after subtracting about 20.00 units for the monomeric repeating unit structures (M1) and (M3), about 53.5 units remain which would belong to the contribution of the 9 hydrogen atoms of the monomeric repeating unit structure (M2).

The ratio of the monomeric repeating unit structures (M1):(M3):(M2) for a single hydrogen is thus about 1:1:(53.5/9), that is, about 1.00:1.00:5.94. This is almost identical to the feed ratio of about 1:1:6.

Example 3: Synthesis of Acrylamide-Based Bipolymers Having General Formula (I)

Materials and Methods.

Acrylamide-based bipolymers having General Formula (I) in which $R^1$ is methyl, $R^2$ is methyl, $R^3$ is not present, $R^4$ is —$(CH_2)_5$—, x is 0.5, y is 0, and z is 0.5, were synthesized in accordance with the following reaction scheme:

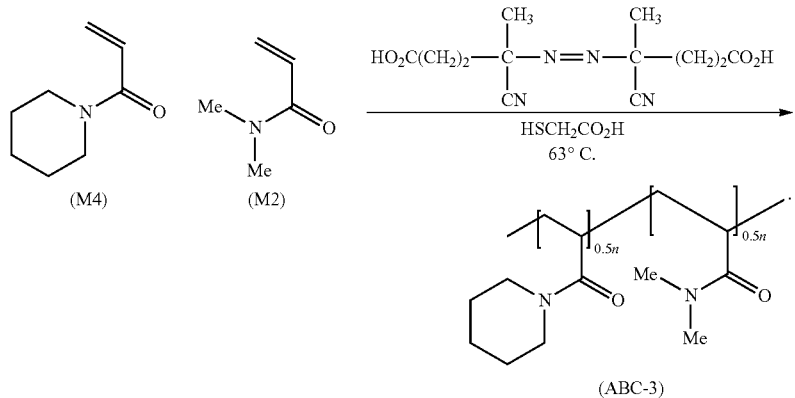

More specifically, acrylamide-based bipolymers having General Formula (I) were synthesized by adding ABCVA (about 350 mg, 1.25 mmol) to a solution having a monomeric repeating unit of structure (M4) (about 36 mmol):

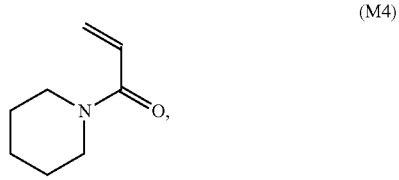

a monomeric repeating unit of structure (M2) (about 36 mmol):

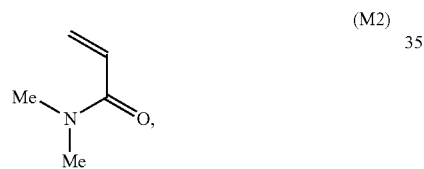

and
thioglycolic acid (about 166 mg, 1.80 mmol) in water (about 42 mL) under $N_2$ to form a reaction mixture.

The reaction mixture was stirred under $N_2$ at about 63° C. using a magnetic stir-bar for 24 hours. Within a few hours, a cloudy suspension was observed. While cloudy at about 63° C., the reaction mixture was clear at room temperature, thus implying that the bipolymers of General Formula (I) had an LCST. After 24 hours, the reaction mixture was heterogeneous and cooled to room temperature to obtain a clear solution. The clear solution was then washed with petroleum ether (about 3×20 mL) and freeze-dried to obtain an acrylamide-based bipolymer of structure (ABC-3):

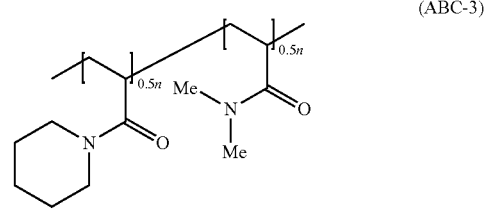

as a white polymer (Yield: about 85%).

Results.

Figure 3:
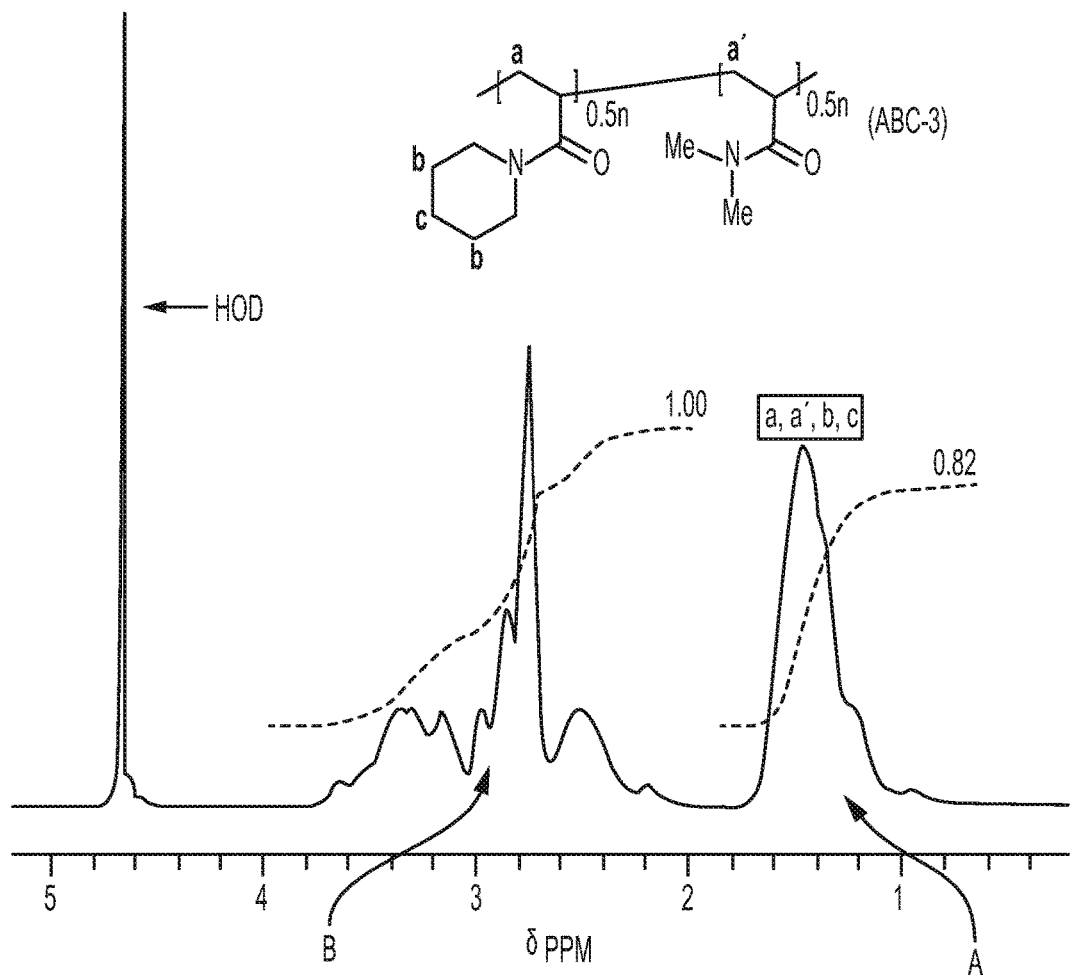
FIG. 3 is a $^1$H NMR spectrum of acrylamide-based copolymers having structure (ABC-3) as disclosed in Table 1, where the area (A) corresponds to the area under Chemical Shift δ=0.8-1.8 ppm belonging to the 10 hydrogen atoms marked a, a', b, and c in structure (ABC-3), and where the area (B) corresponds to the area under δ 2.0-3.8 ppm belonging to the remaining 12 unmarked hydrogen atoms.

The $^1$H NMR spectrum was carefully analyzed to determine the composition of the bipolymer of structure (ABC-3). For example, referencing FIG. 3, for a ratio of about 1:1 of the incorporated monomeric repeating units of structures (M4) and (M2), the area (A) under about δ 0.8-1.8 ppm would belong to the 10 Hs marked a, a', b and c, while the area (B) of the rest of the 12 unmarked protons appearing in the range of about δ 2.0-3.8 would thus amount to (A/10)× 12. The area ratio B/A would thus equal about [(A/10)×12]/ A, that is, about 1.20. The experimental ratio of monomeric repeating unit structures (M4):(M2) is about 1.00/0.82, that is, about 1.22. Thus, the ascertained the bipolymer composition of monomeric repeating unit structures (M4):(M2) is about 1:1.

Example 4: Synthesis of Acrylamide-Based Bipolymers Having General Formula (I)

Materials and Methods.

Acrylamide-based bipolymers having General Formula (I) in which $R^1$ is methyl, $R^2$ is methyl, $R^3$ is not present, $R^4$ is —$(CH_2)_4$—, x is 0.75, y is 0, and z is 0.25, were synthesized as in Example 3 except as indicated otherwise. More specifically, acrylamide-based bipolymers having General Formula (I) were synthesized by adding ABCVA (about 350 mg, 1.25 mmol) to a solution having a monomeric repeating unit of structure (M4) (about 18 mmol):

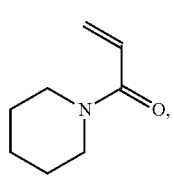

a monomeric repeating unit of structure (M2) (about 54 mmol):

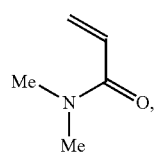

and thioglycolic acid (about 166 mg, 1.80 mmol) in water (about 42 mL) under $N_2$ to form a reaction mixture.

The reaction mixture was stirred under $N_2$ at about 63° C. using a magnetic stir-bar for 24 hours. After 24 hours, the reaction mixture was cooled to room temperature. The reaction mixture was then washed with petroleum ether (about 3×20 mL) and freeze-dried to obtain an acrylamide-based bipolymer of structure (ABC-4):

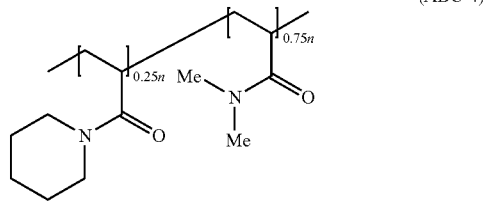

(ABC-4)

as a white polymer (Yield: about 85%).

Results.

Figure 4:
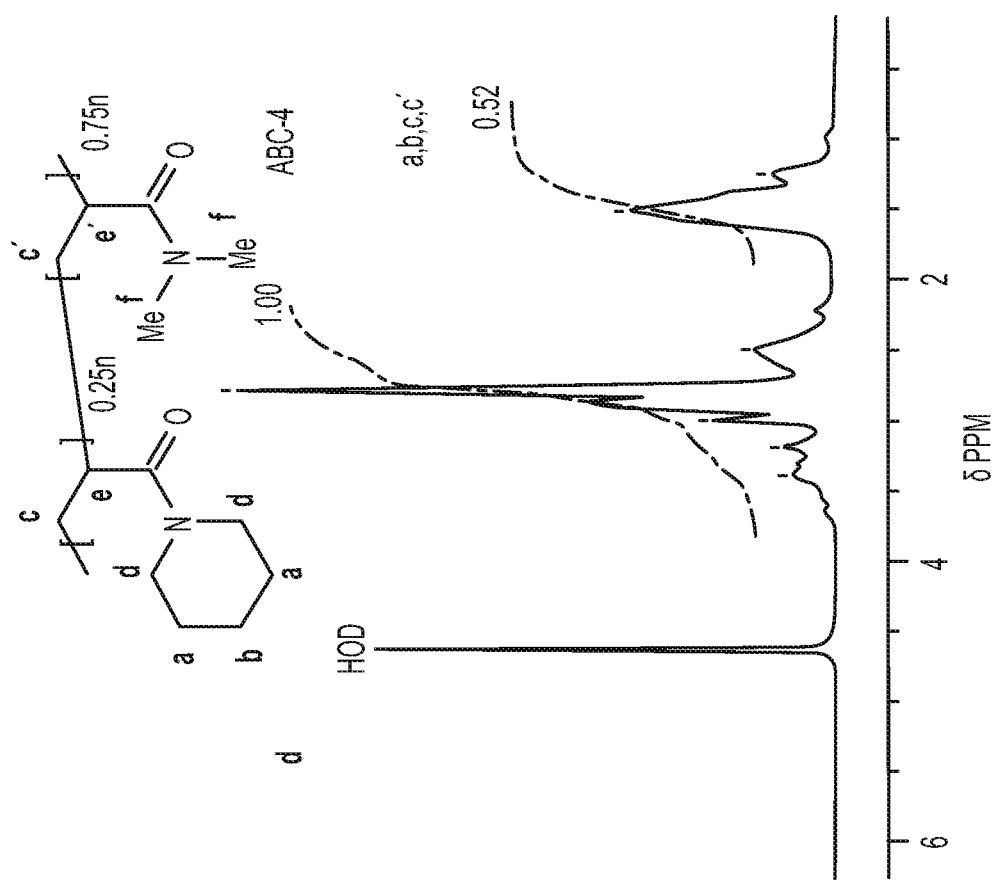
FIG. 4 is a $^1$H NMR spectrum of acrylamide-based copolymers having structure (ABC-4) as disclosed in Table 1, where the area under Chemical Shift δ=0.9-1.75 ppm belongs to the 8 hydrogen atoms marked a, b, and c in monomeric repeating unit structure (M4) and has an integrated area of 8y, where the 2 hydrogen atoms marked c' in monomeric repeating structure (M2) have an integrated area of 6y (that is, 2*3y), the total integrated area for the hydrogen atoms marked a, b, c, and c' is 14y, where the area under δ 2.0-3.7 ppm belongs to the hydrogen atoms marked d and e and accounts for 5y, and where the integrated area for hydrogen atoms marked e' and f is 21 y (that is, 7*3y)

The bipolymer of structure (ABC-4) did not show a LCST in the range 20° C. to 63° C. For example, referencing FIG. 4, for a ratio of about 1:3 of the incorporated monomeric repeating units of structures (M4) and (M2), the area under about δ 0.9-1.75 ppm would belong to the 8 hydrogen atoms marked a, b, and c in monomeric repeating unit structure (M4) and would have an integrated area of about 8y, the 2 hydrogen atoms marked c' in monomeric repeating unit (M2) would have an integrated area of about 6y (that is, about 2*3y), the hydrogen atoms marked a, b, c, and c' in the monomeric repeating unit structures (M2) and (M4) would have an integrated area of about 14y, the area under about δ 2.0-3.7 ppm would belong to the hydrogen atoms marked d and e in the monomeric repeating unit structure (M4) and accounts for about 5y, and the hydrogen atoms marked e' and f would have an integrated area of about 21y (that is, about 7*3y). The total integrated area of the protons marked d, e, e', and f should be about 26y (that is, 5y+21y). Thus, the ratio of the areas in the ranges of about δ 2.0-3.7 ppm and about δ 0.9-1.75 ppm should be about 1.86 (that is, 26y/14y). The observed area ratio of monomeric repeating unit structures (M4):(M2) is about 1.92 (that is, about 1.00/0.52). This confirms the feed ratio of about 1:2.

Example 5: Synthesis of Acrylamide-Based Bipolymers Having General Formula (I)

Materials and Methods.

Acrylamide-based bipolymers having General Formula (I) in which $R^1$ is not present, $R^2$ is not present, $R^3$ is isopropyl, $R^4$ is —$(CH_2)_5$—, x is 0, y is 0.5, and z is 0.5, were synthesized in accordance with the following reaction scheme:

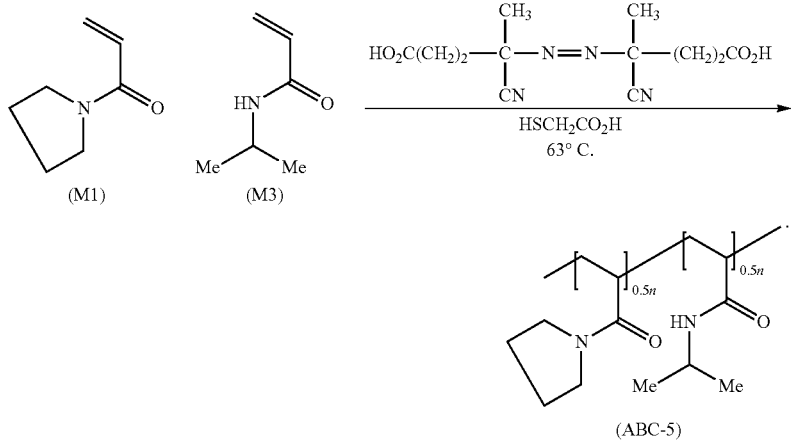

More specifically, acrylamide-based bipolymers having General Formula (I) were synthesized by adding ABCVA (about 350 mg, 1.25 mmol) to a solution having a monomeric repeating unit of structure (M1) (about 36 mmol):

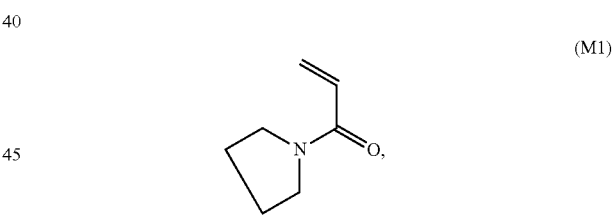

(M1)

a monomeric repeating unit of structure (M3) (about 36 mmol):

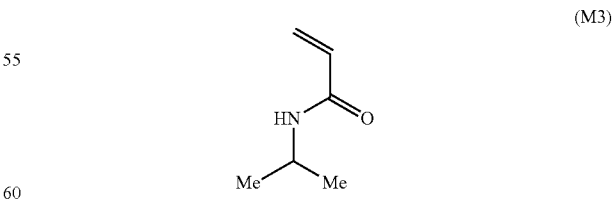

(M3)

and thioglycolic acid (about 334 mg, 3.6 mmol) in water (about 42 mL) under $N_2$ to form a reaction mixture.

The reaction mixture was stirred under $N_2$ at about 63° C. using a magnetic stir-bar for 24 hours. Within a few hours, a cloudy suspension was observed. While cloudy at about 63° C., the reaction mixture was clear at room temperature, thus implying that the bipolymers of General Formula (I) had an LCST. After 24 hours, the reaction mixture was heterogeneous and cooled to room temperature to obtain a clear solution. The clear solution was then washed with petroleum ether (3×20 mL) and freeze-dried to obtain an acrylamide-based bipolymer of structure (ABC-5):

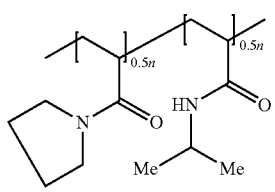
(ABC-5)

as a white polymer (Yield: about 95%).

Results.

Figure 5:
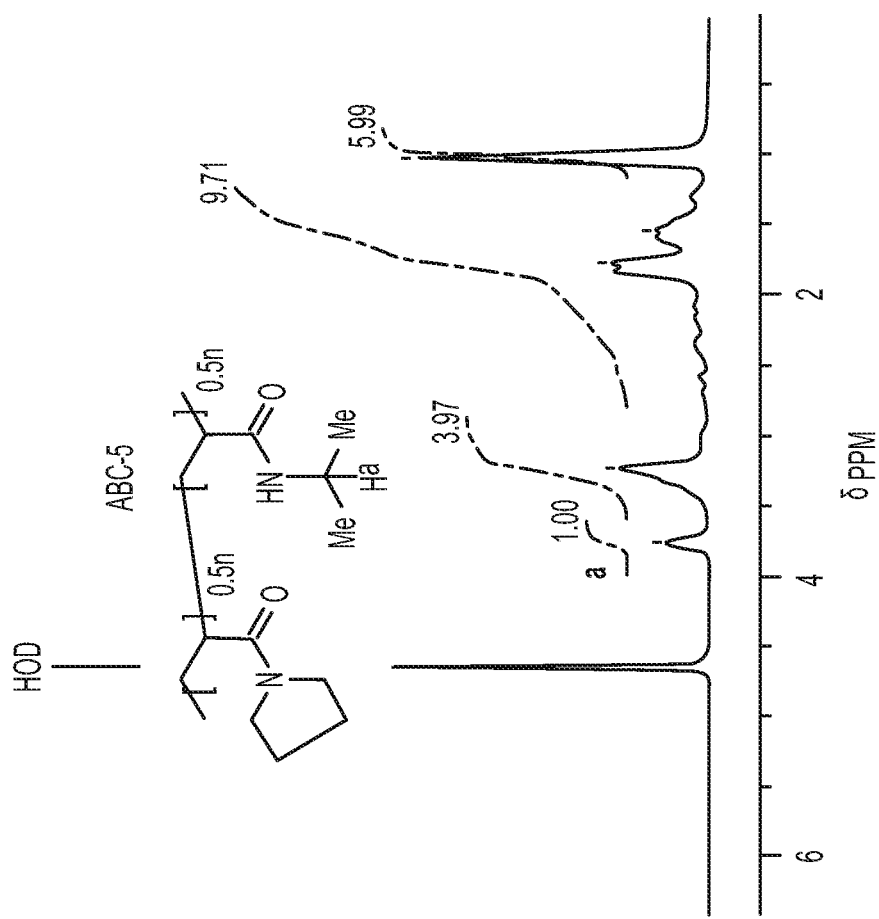
FIG. 5 is a $^1$H NMR spectrum of acrylamide-based copolymers having structure (ABC-5) as disclosed in Table 1, where the area (a) of 1.00 units belongs to the hydrogen atom marked H$^a$ of monomeric repeating unit structure (M3), where the area of 9.00 units under Chemical Shift δ=0.9-3.5 ppm belongs to the remaining non-exchangeable 9 hydrogen atoms of monomeric repeating unit structure (M3), where the total area is 19.67 units (that is, 3.97+9.71+ 5.99), and where 10.67 units belong to the 11 hydrogen atoms of monomeric repeating unit structure (M1)

The LCST of the bipolymer of structure (ABC-5) was found to be 28° C. For example, referencing FIG. 5, for a ratio of 1:1 of the incorporated monomeric repeating units of structures (M1) and (M3), the area (a) of about 1.00 units would belong to the hydrogen atom marked $H^a$ of monomeric repeating unit structure (M3) and the area of about 9.00 units under about δ 0.9-3.5 ppm would belong to the remaining non-exchangeable 9 hydrogen atoms of monomeric repeating unit structure (M3). The total area would be about 19.67 units (that is, about 3.97+9.71+5.99). Additionally, about 10.67 units would belong to the 11 hydrogen atoms of monomeric repeating unit structure (M1). Thus, the area ratio of the incorporated monomeric repeating units of structures (M1):(M3) would be about 10.67/11 (that is, 0.97:1.00), which is almost identical to the feed ratio of about 1:1.

Example 6: Characterization of Acrylamide-Based Terpolymers' (ABT-6) and (ABT-7) Inhibition of Clathrate Hydrate Formation Materials and Methods.

Acrylamide-based terpolymers having General Formula (I) in which $R^1$ is methyl, $R^2$ is methyl, $R^3$ is isopropyl, $R^4$ is —$(CH_2)_5$—, x is 0.40, y is 0.25, and z is 0.35, were synthesized as in Example 1 except as indicated otherwise. More specifically, acrylamide-based terpolymers having General Formula (I) were synthesized by adding ABCVA (about 350 mg, 1.25 mmol) to a solution having a monomeric repeating unit of structure (M4) (about 25.5 mmol):

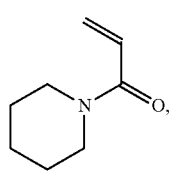
(M4)

a monomeric repeating unit of structure (M3) (about 18 mmol):

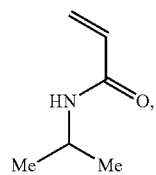
(M3)

a monomeric repeating unit of structure (M2) (about 28.8 mmol):

(M2)

Me, Me thioglycolic acid (about 334 mg, 3.6 mmol) in water (about 42 mL) under $N_2$ to form a reaction mixture.

The reaction mixture was stirred under $N_2$ at about 63° C. using a magnetic stir-bar for 24 hours. After 24 hours, the reaction mixture was homogenous and cooled to room temperature. The reaction mixture was then washed with petroleum ether (about 3×20 mL) and freeze-dried to obtain an acrylamide-based terpolymer of structure (ABT-6):

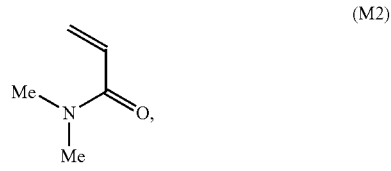
(ABT-6)

(Yield: about 90%)

The composition of acrylamide-based terpolymer of structure (ABT-6) was confirmed via $^1H$ NMR analysis, such as was conducted with regard to acrylamide-based terpolymers of structures (ABT-1) and (ABT-2) in Examples 1 and 2.

Acrylamide-based terpolymers having General Formula (I) in which $R^1$ is methyl, $R^2$ is methyl, $R^3$ is isopropyl, $R^4$ is —$(CH_2)_5$—, x is 0.25, y is 0.25, and z is 0.5, were also synthesized as described with regard to acrylamide-based terpolymer of structure (ABT-6), except that the molar fractions of x, y, and z and the corresponding monomeric repeating units were modified to obtain an acrylamide-based terpolymer of structure (ABT-7). Specifically, acrylamide-based terpolymers having General Formula (I) were synthesized by adding ABCVA (about 350 mg, 1.25 mmol) to a solution having a monomeric repeating unit of structure (M4) (about 36 mmol):

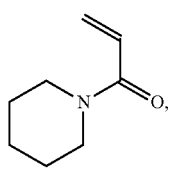

(M4)

a monomeric repeating unit of structure (M3) (about 18 mmol):

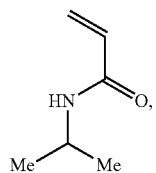

(M3)

a monomeric repeating unit of structure (M2) (about 18 mmol):

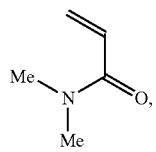

(M2)

thioglycolic acid (about 334 mg, 3.6 mmol) in water (about 42 mL) under $N_2$ to form a reaction mixture.

The reaction mixture was stirred under $N_2$ at about 63° C. using a magnetic stir-bar for 24 hours. After 24 hours, the reaction mixture was homogenous and cooled to room temperature. The reaction mixture was then washed with petroleum ether (about 3×20 mL) and freeze-dried to obtain an acrylamide-based terpolymer of structure (ABT-7):

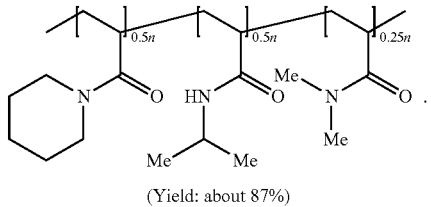

(ABT-7)

(Yield: about 87%)

The composition of acrylamide-based terpolymer of structure (ABT-7) was confirmed via $^1H$ NMR analysis, such as was conducted with regard to acrylamide-based terpolymers of structures (ABT-1) and (ABT-2) in Examples 1 and 2.

The ability of (ABT-6) and (ABT-7) to inhibit clathrate hydrate formation was characterized. More specifically, Rocking Cells (that is, RC-5) were employed to characterize the ability of acrylamide-based terpolymers having structures (ABT-6) and (ABT-7) to inhibit clathrate hydrate formation. The RC-5 included five Hastelloy cells (PSL Systemtechnik Gmbh, Osterode am Harz, Germany) capable of operating under high pressure (that is, up to 200 bars) and in sour gas conditions. The five Hastelloy cells of the RC-5 were immersed in a temperature controlled bath containing ethylene glycol and water. During operation, the RC-5 was rocked to achieve mixing of the reactant slurry. The volume of the Hastelloy cell with a mixing ball was about 30 mL. The RC-5 enabled formation of natural gas clathrate hydrates under simulated operating conditions to test the effectiveness of the acrylamide-based terpolymers having structures (ABT-6) and (ABT-7). Data acquisition was completed with WinRC software to measure the pressure and temperature with time in each of the five Hastelloy cells.

In a typical run simulating pipeline operating conditions in the field, each of the five Hastelloy cells was charged with about 10 mL of an acrylamide-based copolymer formulation. Specifically, the 10 mL acrylamide-based copolymer formulation included an acrylamide-based copolymer (about 0.105 g, about 3 weight %), a solvent (about 0.195 g monoethylene glycol, that is, MEG), and brine (about 9.7 g, about 97 weight %), as set forth in Table 2. Then, the five Hastelloy cells were charged with a natural gas, as described in Table 3, that is, a natural gas was added to the five Hastelloy cells, to a pressure of about 140 bars at 21° C. The brine included an aqueous solution of chloride anions, sodium cations, acetic acid, formic acid, and conjugate bases as set forth in Table 2:

TABLE 2

| Brine | | |
|---|---|---|
| Ion/Molecular Formula | Common Name | Concentration (mg/L) |
| $Cl^-$ | Chloride Anions | 607 |
| $Na^+$ | Sodium Cations | 393 |
| $CH_3COOH$ | Acetic Acid | 500 |
| $HCOOH$ | Formic Acid | 250 |

Because natural gas in the field contains large amounts of methane, carbon dioxide, hydrogen sulfide, and nitrogen and also contains small amounts of ethane, propane, and butane, to simulate pipeline operating conditions in the field, a natural gas composition as set forth in Table 3 was employed:

TABLE 3

| Natural Gas Composition | | |
|---|---|---|
| Molecular Formula | Common Name | Mole % |
| $CH_4$ | Methane | 79.6 |
| $C_2H_6$ | Ethane | 1.4 |
| $C_3H_8$ | Propane | 0.2 |
| $C_4H_{10}$ | Butane | 0.1 |
| $CO_2$ | Carbon Dioxide | 9.2 |
| $H_2S$ | Hydrogen Sulfide | 2.3 |
| $N_2$ | Nitrogen | 7.2 |

Figure 6:
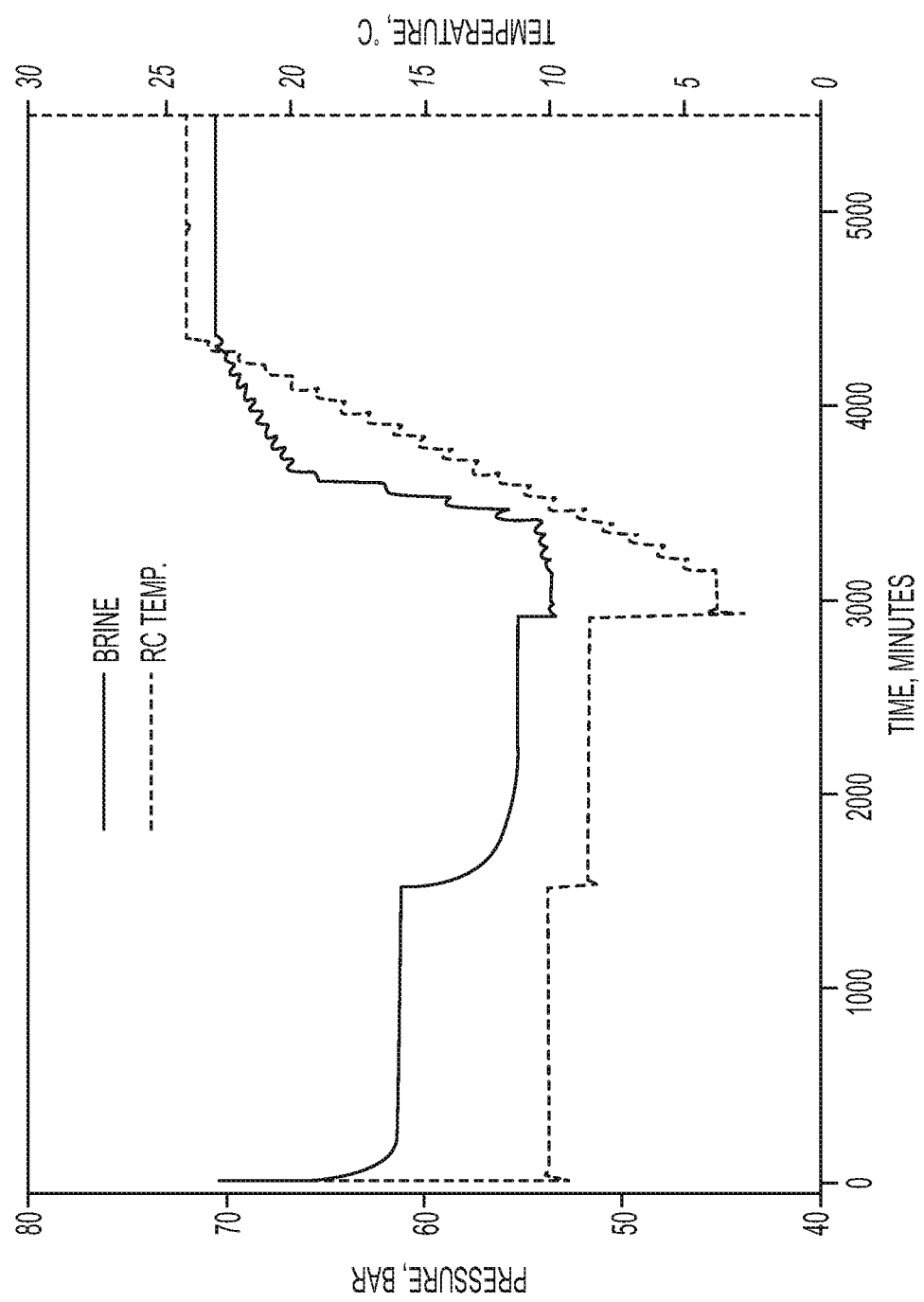
FIG. 6 is a graph of Time (Minutes) with respect to Pressure (Bar) of Brine (that is, Brine) and a graph of Time (Minutes) with respect to Temperature (degrees Celsius, that is ° C.) of Rocking Cells RC-5 (that is, RC Temp.), where the Temperature (° C.) of the Rocking Cells RC-5 is programmed to change in three stages in accordance with the Starting Temperature (° C.), Average Ramp (° C./minute) and Duration (Minutes) as set forth in Table 4.

Then, in this specific Example, each of the five Hastelloy cells were charged with 10 mL of an acrylamide-based copolymer formulation including acrylamide-based terpolymers having structures (ABT-6, about 3 weight %) or (ABT-7, about 3 weight %) and the brine (about 97 weight %) of Table 2. Each acrylamide-based terpolymer structure was tested separately, that is, two different acrylamide-based terpolymer structures were not paired together in a single test. Then, the five Hastelloy cells were charged with a natural gas, as described in Table 3, to a pressure of about 140 bars at 21° C. Referencing FIG. 6, the RC-5 was then programmed to change temperature at three operation stages as set forth generally in Table 4:

TABLE 4

Programmed Temperature Stages in the RC-5 - Program 1

| Stage | Start Temp (° C.) | Average Ramp (° C./min) | $T_{sc}$ (° C./min) | Duration (min) |
|---|---|---|---|---|
| 1 | 14.6 | 0.1 | 4 | 1450 |
| 2 | 13 | 0.1 | 5.6 | 1450 (from 1450 to 2900) |
| 3 | 8.1 | 0.08 | 10.5 | 1000-3000 (from 2900 to 3900-5900) |

The three-phase equilibrium temperature (that is, liquid, vapor, and hydrate) of clathrate hydrates in the natural gas composition of Table 3 was calculated via methods known to those of ordinary skill in the art. The three-phase equilibrium temperature of clathrate hydrates in the natural gas composition was found to be about 18.6° C. at 140 bars. Moreover, the pressure changes for liquid, vapor, and hydrate phases were accounted for by employing a mass balance of the natural gas composition so that pressure changes were accurately attributed to clathrate hydrate formation.

The ability of acrylamide-based terpolymers having structures (ABT-6) and (ABT-7) to inhibit clathrate hydrate formation was evaluated at three subcooling temperatures: about 4.0° C., 5.6° C., and 10.5° C. The ability of acrylamide-based terpolymers having structures (ABT-6) and (ABT-7) to inhibit clathrate hydrate formation was evaluated at three subcooling temperatures to determine the induction period and the temperature at which clathrate hydrate formation occurred. More specifically, in embodiments, the ability of acrylamide-based copolymers to inhibit clathrate hydrate formation was evaluated by assessing the pressure during each of the operation stages at the various subcooling temperatures, where a stable pressure was determined to be indicative of clathrate hydrate inhibition.

Results.

Figure 7:
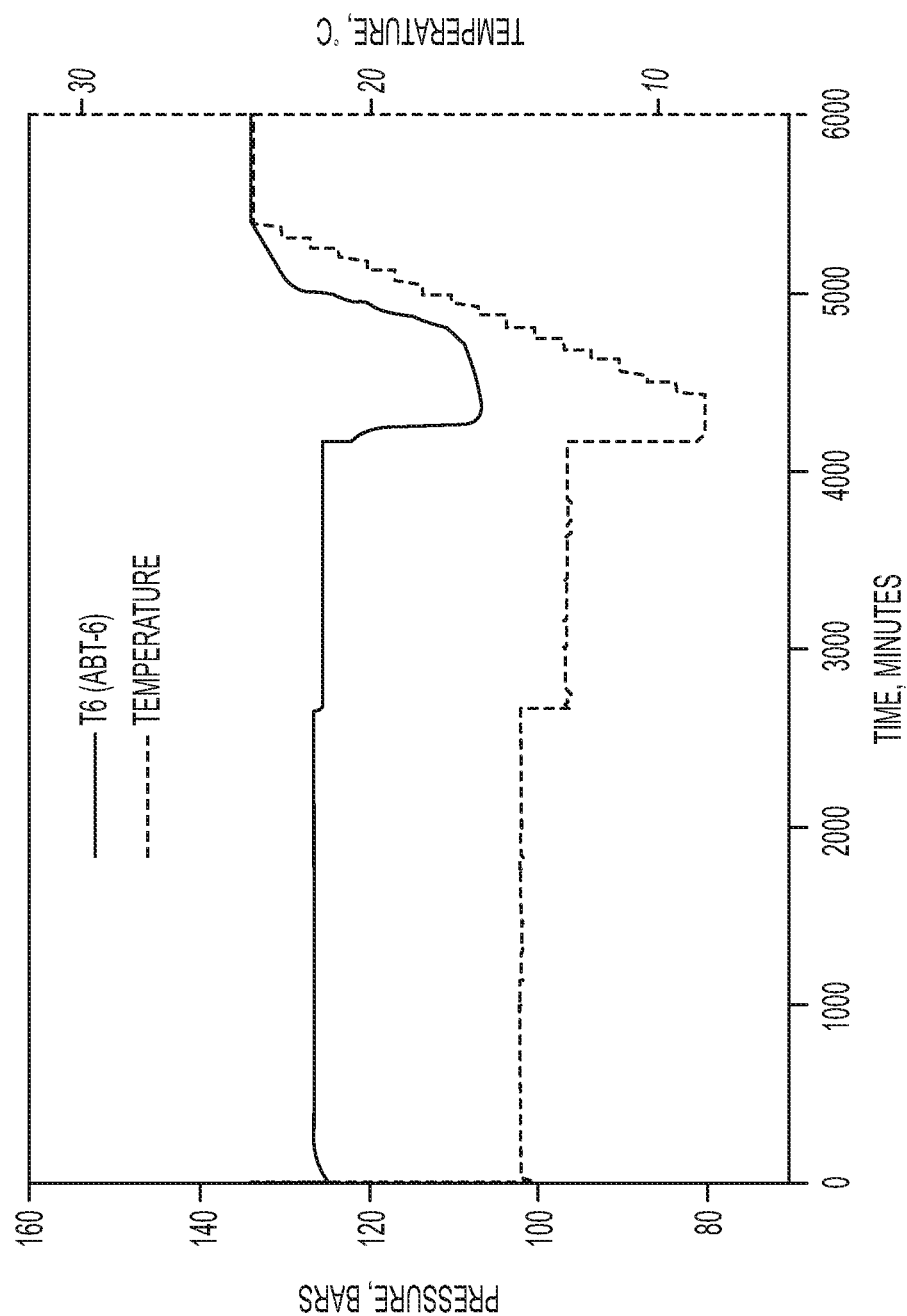
FIG. 7 is a graph of Time (Minutes) with respect to Pressure (Bars) of acrylamide-based terpolymers having structure (ABT-6) (that is, T6) as disclosed in Table 1, and a graph of Time (Minutes) with respect to Temperature (° C.) of Rocking Cells RC-5 (that is, Temperature), where the Temperature (° C.) of the Rocking Cells RC-5 is programmed to change in three stages in accordance with the Starting Temperature (° C.), Average Ramp (° C./minute) and Duration (Minutes) as set forth in Table 4.

As shown in FIG. 7, the acrylamide-based terpolymer having structure (ABT-6) was an effective inhibitor of clathrate hydrate formation at both a first subcooling temperature of 4.0° C. and a second subcooling temperature of 5.6° C. In contrast, the acrylamide-based terpolymer having structure (ABT-7) was an effective hydrate inhibitor of clathrate hydrate formation at a first subcooling temperature 4.0° C.

Example 7: Characterization of Ability of Acrylamide-Based Terpolymers (ABT-1) and (ABT-2) to Inhibit Clathrate Hydrate Formation Materials and Methods.

Acrylamide-based terpolymers having structures (ABT-1) and (ABT-2) were synthesized as in Examples 1-2. The ability of (ABT-1) and (ABT-2) to inhibit clathrate hydrate formation was characterized as in Example 6, except as otherwise indicated. Specifically, each of the five Hastelloy cells was charged with about 10 mL of an acrylamide-based copolymer formulation. Specifically, the 10 mL acrylamide-based copolymer formulation included an acrylamide-based copolymer (about 1 weight %), a solvent (about 2 weight % MEG), and brine (about 97 weight %), as set forth in Table 2.

Results.

Figure 8:
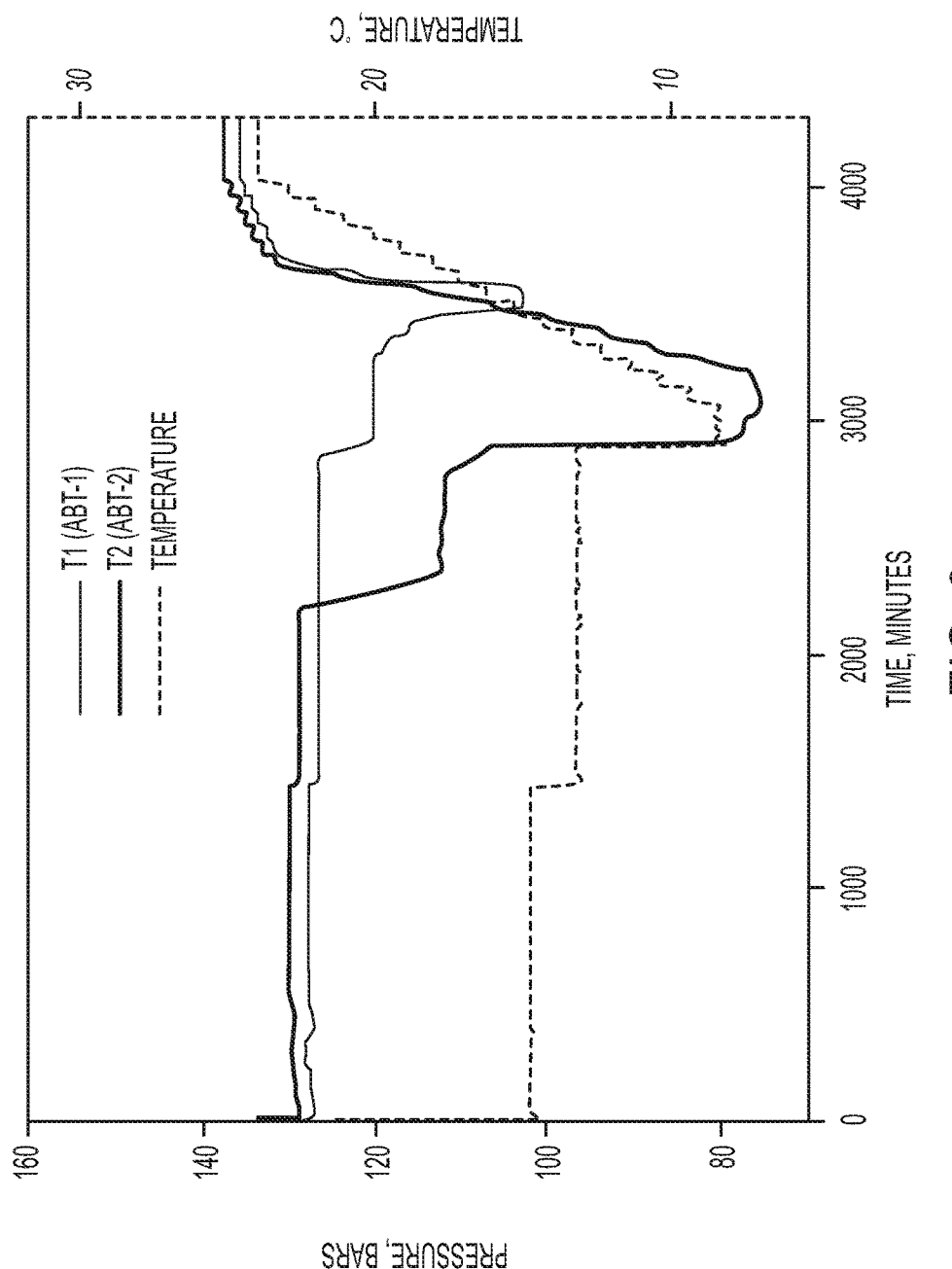
FIG. 8 is a graph of Time (Minutes) with respect to Pressure (Bars) of acrylamide-based terpolymers having structures (ABT-1) (that is, T1) and (ABT-2) (that is, T2) as disclosed in Table 1, and a graph of Time (Minutes) with respect to Temperature (° C.) of Rocking Cells RC-5 (that is, Temperature), where the Temperature (° C.) of the Rocking Cells RC-5 is programmed to change in three stages in accordance with the Starting Temperature (° C.), Average Ramp (° C./minute) and Duration (Minutes) as set forth in Table 4.

As shown in FIG. 8, the acrylamide-based terpolymer having structure (ABT-1) was an effective inhibitor of clathrate hydrate formation at both a first subcooling temperature of 4.0° C. and a second subcooling temperature of 5.6° C. Additionally, the acrylamide-based terpolymer having structure (ABT-2) was an effective inhibitor of clathrate hydrate formation at a first subcooling temperature of 4.0° C.

Example 8: Characterization of Ability of Acrylamide-Based Bipolymers' (ABC-3) and (ABC-4) to Inhibit Clathrate Hydrate Formation Materials and Methods.

Acrylamide-based bipolymers having structures (ABC-3) and (ABC-4) were synthesized as in Examples 3-4. The ability of (ABC-3) and (ABC-4) to inhibit clathrate hydrate formation was characterized as in Example 6, except as otherwise indicated. Specifically, each of the five Hastelloy cells was charged with about 10 mL of an acrylamide-based copolymer formulation. Specifically, the 10 mL acrylamide-based copolymer formulation included an acrylamide-based copolymer (about 1 weight %), a solvent (about 2 weight % MEG), and a brine (about 97 weight %), as set forth in Table 2. Additionally, the RC-5 was programmed to change temperature at three operation stages as set forth generally in Table 5:

TABLE 5

Programmed Temperature Stages in the RC-5 - Program 2

| Stage | Start Temp (° C.) | Average Ramp (° C./min) | $T_{sc}$ (° C./min) | Duration (min) |
|---|---|---|---|---|
| 1 | 14.6 | 0.1 | 4 | 7000 |
| 2 | 13 | 0.1 | 5.6 | 1500 (from 7000 to 8500) |
| 3 | 8.1 | 0.08 | 10.5 | 2500 (from 8500 to 11000) |

Results.

Figure 9:
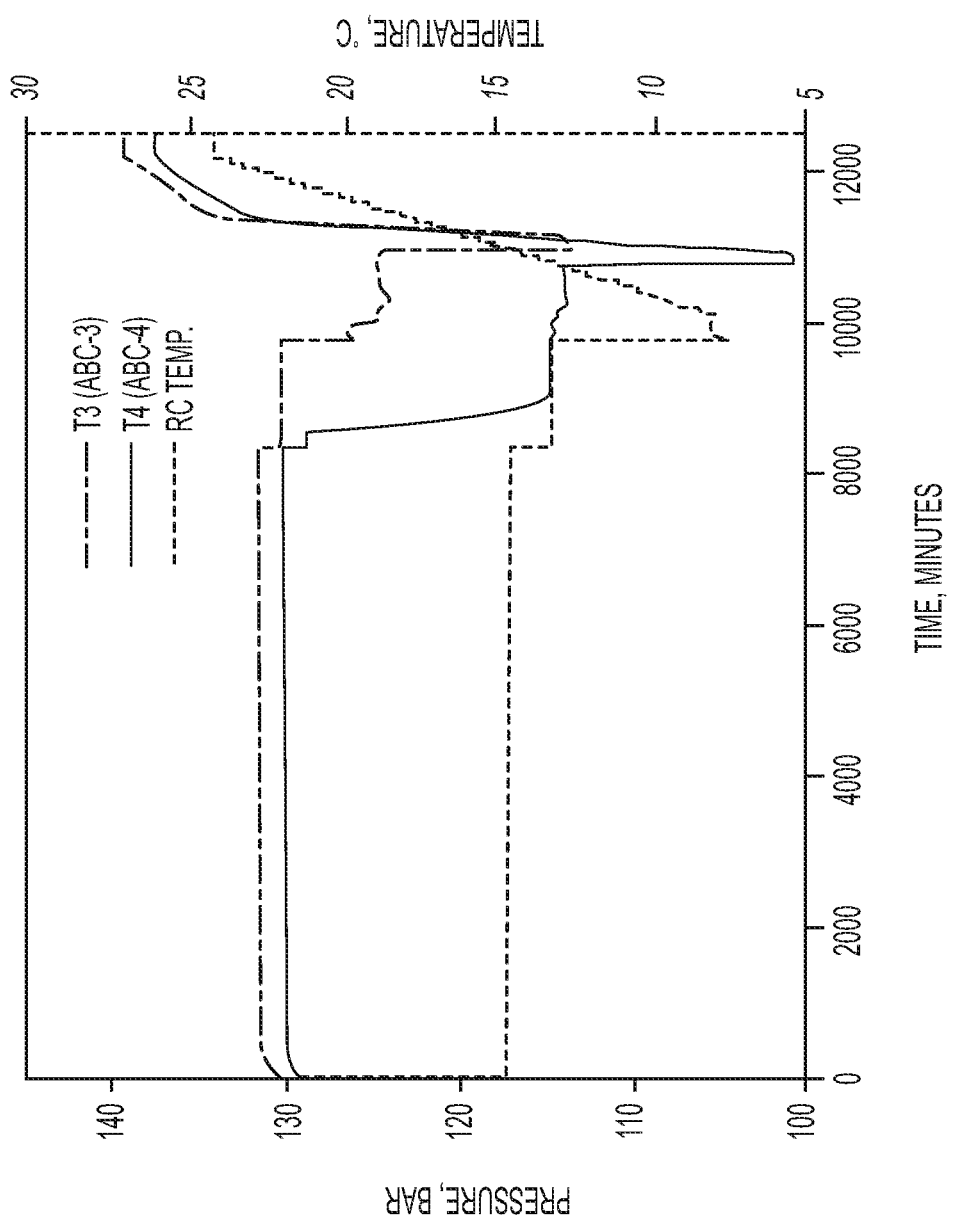
FIG. 9 is a graph of Time (Minutes) with respect to Pressure (Bar) of acrylamide-based copolymers having structures (ABC-3) (that is, T3) and (ABC-4) (that is, T4) as disclosed in Table 1, and a graph of Time (Minutes) with respect to Temperature (° C.) of Rocking Cells RC-5 (that is, RC Temp.), where the Temperature (° C.) of the Rocking Cells RC-5 is programmed to change in three stages in accordance with the Starting Temperature (° C.), Average Ramp (° C./minute) and Duration (Minutes) as set forth in Table 5.

As shown in FIG. 9, the acrylamide-based bipolymer having structure (ABC-3) was an effective inhibitor of clathrate hydrate formation at both a first subcooling temperature of 4.0° C. and a second subcooling temperature of 5.6° C. Additionally, the acrylamide-based bipolymer having structure (ABC-4) was an effective inhibitor of clathrate hydrate formation at a first subcooling temperature of 4.0° C.

Example 9: Characterization of Ability of Acrylamide-Based Bipolymers Having Structures (ABC-5) and (ABC-8) to Inhibit Clathrate Hydrate Formation Materials and Methods.

Acrylamide-based bipolymers having General Formula (I) in which $R^1$ is not present, $R^2$ is not present, $R^3$ is isopropyl, $R^4$ is —$(CH_2)_4$—, x is 0, y is 0.5, and z is 0.5 (ABC-5) were synthesized as in Example 5. Acrylamide-based bipolymers having General Formula (I) in which $R^1$ is methyl, $R^2$ is methyl, $R^3$ is not present, $R^4$ is —$(CH_2)_4$—, x is 0.5, y is 0, and z is 0.5 (ABC-8), were also synthesized as in Example 1 except as indicated otherwise. More specifically, acrylamide-based bipolymers having structure (ABC- 8) were synthesized by adding ABCVA to a solution having a monomeric repeating unit of structure (M1) (about 36 mmol):

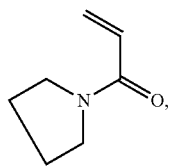
(M1)

a monomeric repeating unit of structure (M2) (about 36 mmol):

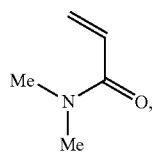
(M2)

thioglycolic acid (about 5.2 mmol) in water (about 42 mL) under N₂ to form a reaction mixture. The reaction mixture was stirred under N₂ at about 63° C. using a magnetic stir-bar for 24 hours. After 24 hours, the reaction mixture was homogenous and cooled to room temperature. The reaction mixture was then washed with petroleum ether and freeze-dried to obtain an acrylamide-based bipolymer of structure (ABC-8):

lp;-1p

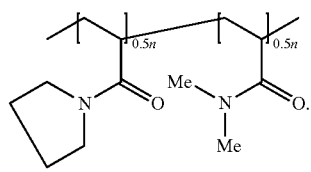
(ABC-8)

The ability of (ABC-5) and (ABC-8) to inhibit clathrate hydrate formation was characterized as in Example 6, except as otherwise indicated. Specifically, each of the five Hastelloy cells was charged with about 10 mL of an acrylamide-based copolymer formulation. Specifically, the 10 mL acrylamide-based copolymer formulation included an acrylamide-based copolymer (about 1 weight %), a solvent (about 2 weight % MEG), and brine (about 97 weight %), as set forth in Table 2.

Results.

Figure 10:
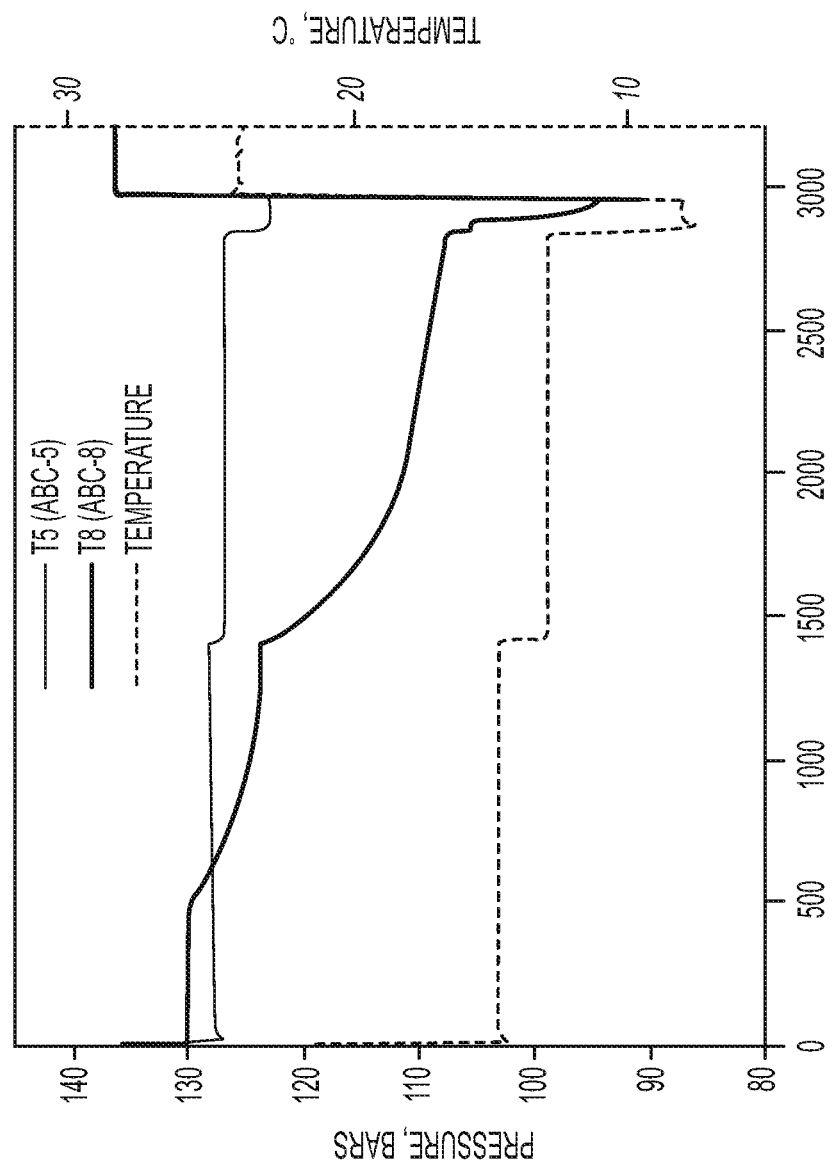
FIG. 10 is a graph of Time (Minutes) with respect to Pressure (Bars) of acrylamide-based copolymers having structures (ABC-5) (that is, T5) and (ABC-8) (that is, T8) as disclosed in Table 1, and a graph of Time (Minutes) with respect to Temperature (° C.) of Rocking Cells RC-5 (that is, TC Temp.) where the Temperature (° C.) of the Rocking Cells RC-5 is programmed to change in three stages in accordance with the Starting Temperature (° C.), Average Ramp (° C./minute) and Duration (Minutes) as set forth in Table 4.

As shown in FIG. 10, the acrylamide-based bipolymer having structure (ABC-5) was an effective inhibitor of clathrate hydrate formation at both a first subcooling temperature of 4.0° C. and a second subcooling temperature of 5.6° C. In contrast, the acrylamide-based bipolymer having structure (ABC-8) was an effective inhibitor of clathrate hydrate formation for a few hours at a first subcooling temperature of 4.0° C.

Example 10: Characterization of Ability of Acrylamide-Based Homopolymers Having Structures (ABH-1) and (ABH-2) to Inhibit Clathrate Hydrate Formation Materials and Methods.

Acrylamide-based homopolymers (that is, ABH) having structures (ABH-1), (ABH-2), (ABH-3), and (ABH-4) were synthesized. More specifically, acrylamide-based homopolymers having structures (ABH-1), (ABH-2), (ABH-3), and (ABH-4) were synthesized from the corresponding monomeric repeating units of structures (M5), (M3), (M2), and (M1), respectively, as in Example 1 except as indicated otherwise. (Yield: about 85-93%). In synthesizing the acrylamide-based homopolymers having structures (ABH-1), (ABH-2), (ABH-3), and (ABH-4), about 72 mmol of the corresponding monomeric repeating units of structures (M5), (M3), (M2), and (M1) was employed. The monomeric repeating unit of structure (M5) is shown:

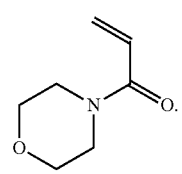
(M5)

The acrylamide-based homopolymers having structures (ABH-1), (ABH-2), (ABH-3), and (ABH-4) are shown:

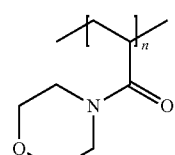
(ABH-1)

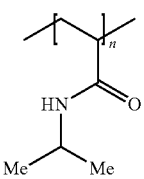
(ABH-2)

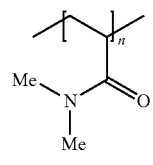
(ABH-3)

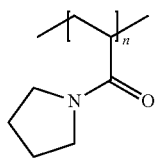
(ABH-4)

The ability of (ABH-1), (ABH-2), (ABH-3), and (ABH-4) to inhibit clathrate hydrate formation was characterized as in Example 6, except as otherwise indicated. Specifically, each of the five Hastelloy cells was charged with about 10 mL of an acrylamide-based copolymer formulation. Specifically, the 10 mL acrylamide-based copolymer formulation included an acrylamide-based copolymer (about 1 weight %), a solvent (about 2 weight % MEG), and brine (about 97 weight %), as set forth in Table 2.

Results.

Figure 11:
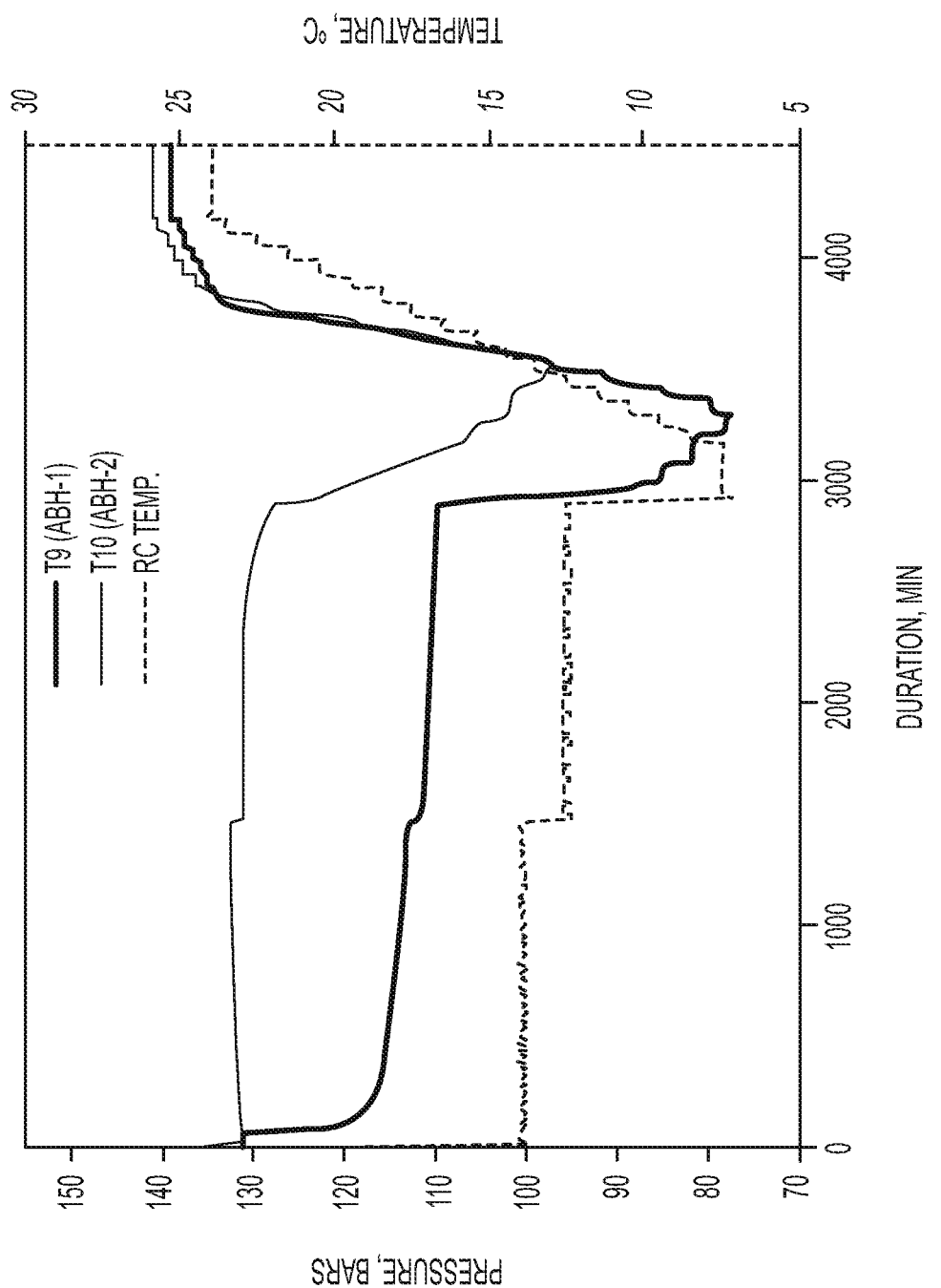
FIG. 11 is a graph of Duration (Minutes, that is, Min) with respect to Pressure (Bars) of acrylamide-based homopolymers having structures (ABH-1) (that is, T9) and (ABH-2) (that is, T10) and a graph of Duration (Min) with respect to Temperature (° C.) of Rocking Cells RC-5 (that is, RC Temp.) where the Temperature (° C.) of the Rocking Cells RC-5 is programmed to change in three stages in accordance with the Starting Temperature (° C.), Average Ramp (° C./minute) and Duration (Min) as set forth in Table 4.
Figure 12:
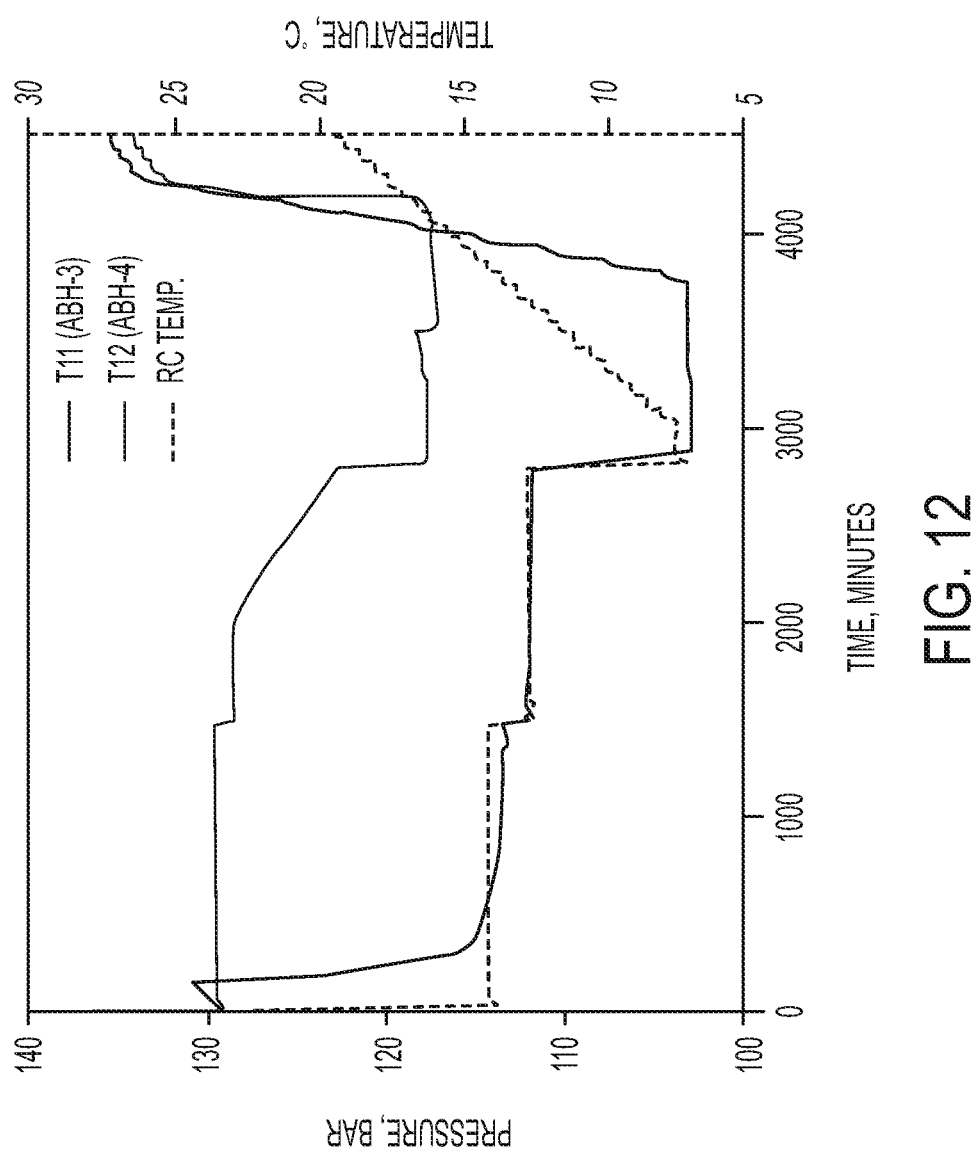
FIG. 12 is a graph of Time (Minutes) with respect to Pressure (Bar) of acrylamide-based homopolymers having structures (ABH-3) (that is, T11) and (ABH-4) (that is, T12) and a graph of Time (Minutes) with respect to Temperature (° C.) of Rocking Cells RC-5 (that is, RC Temp.) where the Temperature (° C.) of the Rocking Cells RC-5 is programmed to change in three stages in accordance with the Starting Temperature (° C.), Average Ramp (° C./minute) and Duration (Minutes) as set forth in Table 4.

As shown in FIGS. 11-12, the acrylamide-based homopolymers having structures (ABH-2) and (ABH-4) was an effective inhibitor of clathrate hydrate formation at a first subcooling temperature of 4.0° C. In contrast, the acrylamide-based homopolymers having structures (ABH-1) and (ABH-3) were not effective inhibitors of clathrate hydrate formation at any subcooling temperatures.

It will be apparent to those skilled in the art that various modifications and variations can be made to the embodiments described in this disclosure without departing from the spirit and scope of the claimed subject matter. Thus it is intended that this disclosure cover the modifications and variations of the various embodiments described provided such modification and variations come within the scope of the appended claims and their equivalents.

It is noted that terms like "generally," "commonly," and "typically" are not utilized to limit the scope of the claims or to imply that certain features are critical, essential, or even important to the structure or function of the claims. Rather, these terms are merely intended to highlight alternative or additional features that may or may not be utilized in a particular embodiment of the present disclosure.

It is to be further understood that where descriptions of various embodiments use the term "comprising," or "including" those skilled in the art would understand that in some specific instances, an embodiment can be alternatively described using language "consisting essentially of" or "consisting of."

Unless otherwise indicated, all numbers expressing quantities of ingredients, properties such as reaction conditions, and so forth used in the disclosure and claims are to be understood as being modified in all instances by the term "about." Accordingly, unless indicated to the contrary, the numerical parameters set forth in this disclosure and claims are approximations that can vary depending upon the desired properties sought to be obtained by the presently-disclosed subject matter.

It should be understood that every maximum numerical limitation given throughout this disclosure includes every lesser numerical limitation, as if such lesser numerical limitations were expressly written in this disclosure. Every minimum numerical limitation given throughout this disclosure will include every greater numerical limitation, as if such greater numerical limitations were expressly written in this disclosure. Every numerical range given throughout this disclosure will include every narrower numerical range that falls within such broader numerical range, as if such narrower numerical ranges were all expressly written in this disclosure.

Unless otherwise defined, all technical and scientific terms used in this disclosure have the same meaning as commonly understood by one of ordinary skill in the art to which the claimed subject matter belongs. The terminology used in this disclosure is for describing particular embodiments only and is not intended to be limiting. As used in the disclosure and appended claims, the singular forms "a," "an," and "the" are intended to include the plural forms as well, unless the context clearly indicates otherwise.

What is claimed is:

1. A terpolymer having General Formula (I):

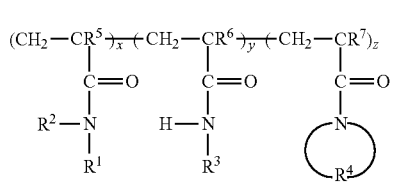

in which:

$R^1$, $R^2$, and $R^3$ are each independently chosen from $C_1$ to $C_8$ saturated aliphatic groups, $R^4$ is chosen from divalent $C_4$ to $C_7$ linear aliphatic groups or divalent $C_4$ to $C_7$ linear heteroaliphatic groups, optionally substituted with one or more $C_1$-$C_6$ linear aliphatic groups, $C_1$-$C_6$ branched aliphatic groups, or combination thereof, where the divalent $C_4$ to $C_7$ linear heteroaliphatic groups comprise 1 or 2 heteroatoms independently chosen from O, N, or S, $R^5$, $R^6$, and $R^7$ are each independently chosen from methyl or hydrogen, x is a molar fraction range chosen from greater than 0 to 0.8, y is a molar fraction range chosen from greater than 0 to 0.8, z is a molar fraction range chosen from 0.1 to 0.9, where the summation of x, y, and z equals 1, and the terpolymer is random.

2. The terpolymer of claim 1, where:

$R^4$ is chosen from divalent $C_4$ to $C_7$ linear aliphatic groups, x is a molar fraction range chosen from greater than 0 to 0.5, y is a molar fraction range chosen from greater than 0 to 0.5, and z is a molar fraction range chosen from 0.2 to 0.75.

3. The terpolymer of claim 1, where:

$R^1$, $R^2$, and $R^3$ are each independently chosen from methyl, ethyl, n-propyl, isopropyl, n-butyl, sec-butyl, isobutyl, tert-butyl, n-pentyl, sec-pentyl, isopentyl, tert-pentyl, n-hexyl, or sec-hexyl, $R^4$ is chosen from divalent $C_4$ to $C_6$ linear aliphatic groups, x is a molar fraction range chosen from greater than 0 to 0.2, y is a molar fraction range chosen from greater than 0 to 0.5, and z is a molar fraction range chosen from 0.2 to 0.75.

4. The terpolymer of claim 1, where

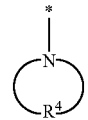

is chosen from

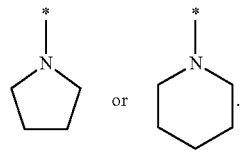

5. The terpolymer of claim 1, where:

$R^1$ is methyl, $R^2$ is methyl, $R^3$ is isopropyl, x is a molar fraction range chosen from 0.5 to 0.75, y is a molar fraction range chosen from 0.1 to 0.25, and z is a molar fraction range chosen from 0.1 to 0.25.

6. The terpolymer of claim 1, where:
x is a molar fraction range chosen from 0.5 to 0.75, and
z is a molar fraction range chosen from 0.25 to 0.5.

7. The terpolymer of claim 1, where the viscosity average molecular weight of the terpolymer is in the range of from 1,000 g/mol to 1,000,000 g/mol.

8. A method for inhibiting formation of clathrate hydrates in a fluid capable of forming the clathrate hydrates, the method comprising:
contacting the fluid with at least one terpolymer of General Formula (I) under conditions suitable for forming the clathrate hydrates:

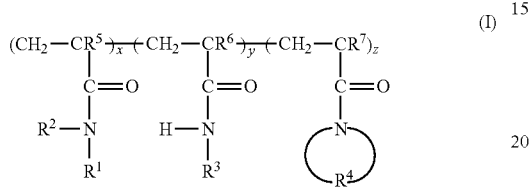
(I)

in which:
$R^1$, $R^2$, and $R^3$ are each independently chosen from $C_1$ to $C_8$ saturated aliphatic groups,
$R^4$ is chosen from divalent $C_4$ to $C_7$ linear aliphatic groups or divalent $C_4$ to $C_7$ linear heteroaliphatic groups, optionally substituted with one or more $C_1$-$C_6$ linear aliphatic groups, $C_1$-$C_6$ branched aliphatic groups, or combination thereof, where the divalent $C_4$ to $C_7$ linear heteroaliphatic groups comprise 1 or 2 heteroatoms independently chosen from O, N, or S,
$R^5$, $R^6$, and $R^7$ are each independently chosen from methyl or hydrogen,
x is a molar fraction range chosen from greater than 0 to 0.8,
y is a molar fraction range chosen from greater than 0 to 0.8,
z is a molar fraction range chosen from 0.1 to 0.9, where the summation of x, y, and z equals 1, and
the at least one terpolymer is random.

9. The method of claim 8, where the fluid comprises water host molecules and natural gas guest molecules chosen from methane, ethane, propane, butane, pentane, carbon dioxide, hydrogen sulfide, nitrogen, or combination thereof.

10. The method of claim 8, where the fluid comprises acid gas guest molecules.

11. The method of claim 8, where:
the clathrate hydrates comprise SI clathrate hydrates, SII clathrate hydrates, or combination thereof and the contacting inhibits formation of the SI clathrate hydrates, the SII clathrate hydrates, or the combination thereof.

12. The method of claim 8, where the contacting inhibits the formation of the clathrate hydrates at a first subcooling temperature of from 0° C. to 4.0° C.

13. The method of claim 8, where the contacting inhibits the formation of the clathrate hydrates in a pressure range of from 40 bars to 200 bars.

14. The method of claim 8, where the fluid is contacted with a composition comprising the at least one terpolymer of Formula (I) and at least one of a corrosion inhibitor or solvent.

15. The method of claim 8, where:
$R^4$ is chosen from divalent $C_4$ to $C_7$ linear aliphatic groups,
x is a molar fraction range chosen from greater than 0 to 0.5,
y is a molar fraction range chosen from greater than 0 to 0.5, and
z is a molar fraction range chosen from 0.2 to 0.75.

16. The method of claim 8, where:
$R^4$ is chosen from divalent $C_4$ to $C_7$ linear aliphatic groups.

17. The method of claim 8, where:

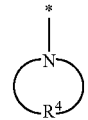

is chosen from

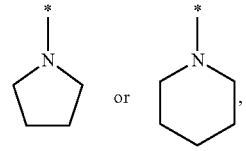

x is a molar fraction range chosen from 0.5 to 0.75,
y is a molar fraction range chosen from 0.1 to 0.25, and
z is a molar fraction range chosen from 0.1 to 0.25.

18. The method of claim 8, where the viscosity average molecular weight of the at least one terpolymer is in the range of from 1,500 g/mol to 20,000 g/mol.

19. The method of claim 8, where the fluid is contacted with the at least one terpolymer at a tie-in platform.

* * * * *